US007670967B2

(12) United States Patent
Runge et al.

(10) Patent No.: US 7,670,967 B2
(45) Date of Patent: *Mar. 2, 2010

(54) DISPERSIBLE ALCOHOL/CLEANING WIPES VIA TOPICAL OR WET-END APPLICATION OF ACRYLAMIDE OR VINYLAMIDE/AMINE POLYMERS

(75) Inventors: Troy Michael Runge, Neenah, WI (US); Richard Warren Tanzer, Neenah, WI (US); Kelly Dean Branham, Woodstock, GA (US); David William Koenig, Menasha, WI (US); Lisa Marie Kroll, Appleton, WI (US); Joseph Mitchell, Alpharetta, GA (US); Michael Ralph Lostocco, Appleton, WI (US); Marlene Ruth Lehman, Greenville, WI (US); William Clayton Bunyard, DePere, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/026,150

(22) Filed: Dec. 30, 2004

(65) Prior Publication Data
US 2006/0003649 A1 Jan. 5, 2006

Related U.S. Application Data

(63) Continuation-in-part of application No. 10/883,192, filed on Jun. 30, 2004.

(51) Int. Cl.
B32B 3/00 (2006.01)
B32B 27/12 (2006.01)
B32B 27/04 (2006.01)
(52) U.S. Cl. .................. 442/59; 442/102; 442/149; 442/417
(58) Field of Classification Search .................. 442/59
See application file for complete search history.

(56) References Cited

U.S. PATENT DOCUMENTS

| 3,415,804 A * | 12/1968 | Polson .................. 530/382 |
| 3,554,788 A | 1/1971 | Fechillas |
| 3,554,862 A | 1/1971 | Hervey et al. |
| 3,989,818 A * | 11/1976 | Polson .................. 424/209.1 |
| 4,144,122 A | 3/1979 | Emanuelsson et al. |
| 4,157,724 A | 6/1979 | Persson |
| 4,186,233 A | 1/1980 | Krajewski et al. |
| 4,264,289 A | 4/1981 | Day |
| 4,278,113 A | 7/1981 | Persson |
| 4,291,087 A | 9/1981 | Warburton, Jr. |
| 4,309,469 A | 1/1982 | Varona |
| 4,343,403 A | 8/1982 | Daniels et al. |
| 4,352,649 A | 10/1982 | Jacobsen et al. |
| 4,353,686 A | 10/1982 | Hosler et al. |
| 4,353,687 A | 10/1982 | Nielsen |
| 4,362,781 A | 12/1982 | Anderson |
| 4,476,323 A | 10/1984 | Hellsten et al. |
| RE31,775 E | 12/1984 | Persson |
| 4,494,278 A | 1/1985 | Kroyer et al. |
| 4,627,806 A | 12/1986 | Johnson |
| 4,640,810 A | 2/1987 | Laursen et al. |
| 4,650,409 A | 3/1987 | Nistri et al. |
| 4,667,890 A | 5/1987 | Gietman, Jr. |
| 4,724,980 A | 2/1988 | Farley |
| 5,017,646 A | 5/1991 | Muramoto et al. |
| 5,145,663 A | 9/1992 | Simmons |
| 5,252,232 A | 10/1993 | Vinod |
| 5,252,332 A | 10/1993 | Goldstein |
| 5,256,417 A | 10/1993 | Koltisko |
| 5,281,306 A | 1/1994 | Kakiuchi et al. |
| 5,312,883 A | 5/1994 | Komatsu et al. |
| 5,317,063 A | 5/1994 | Komatsu et al. |
| 5,384,189 A | 1/1995 | Kuroda et al. |
| 5,399,412 A | 3/1995 | Sudall et al. |
| 5,423,804 A | 6/1995 | Kulick |
| 5,429,686 A | 7/1995 | Chiu et al. |
| 5,441,723 A | 8/1995 | Simmons |
| 5,466,518 A | 11/1995 | Isaac et al. |
| 5,509,913 A | 4/1996 | Yeo |

(Continued)

FOREIGN PATENT DOCUMENTS

EP 0 012 033 A1 6/1980

(Continued)

OTHER PUBLICATIONS

Akashi, Mitsuru et al., "Novel Nonionic and Cationic Hydrogels Prepared from N-Vinylacetamide," *Journal of Polymer Science: Part A: Polymer Chemistry*, vol. 31, John Wiley & Sons, Inc., 1993, pp. 1153-1160.

Akashi, Mitsuru et al., "Synthesis of Poly(N-vinylisobutyramide) from Poly(N-vinylacetamide)," *Journal of Polymer Science: Part A: Polymer Chemistry*, vol. 34, John Wiley & Sons, Inc., 1996, pp. 301-303.

Block, Seymour S., "Surface-Active Agents: Amphoteric Compounds," Chapter 15, *Disinfection, Sterilization, and Preservation*, Fourth Edition, edited by Seymour S. Block, published by Lea & Febiger, 1991, pp. 263-272.

(Continued)

*Primary Examiner*—D. Lawrence Tarazano
*Assistant Examiner*—Altrev C Sykes
(74) *Attorney, Agent, or Firm*—Armstrong Teasdale, LLP

(57) ABSTRACT

The present invention is directed to a wet wipe product. The wet wipe product comprises a fibrous substrate and a triggerable binder formulation. The triggerable binder formulation is capable of binding the fibers in the fibrous substrate. The triggerable binder formulation may include acrylamide polymers, vinylamide/amine polymers, and mixtures. The triggerable binder formulation is insoluble in a wetting composition comprising an insolubilizing agent but is dispersible in disposal water.

40 Claims, No Drawings

U.S. PATENT DOCUMENTS

| | | | |
|---|---|---|---|
| 5,573,637 | A | 11/1996 | Ampulski et al. |
| 5,576,364 | A | 11/1996 | Isaac et al. |
| 5,607,551 | A | 3/1997 | Farrington, Jr. et al. |
| 5,629,081 | A | 5/1997 | Richards et al. |
| 5,672,248 | A | 9/1997 | Wendt et al. |
| 5,958,555 | A | 9/1999 | Takeuchi et al. |
| 5,965,115 | A | 10/1999 | Bolich, Jr. et al. |
| 6,168,782 | B1 * | 1/2001 | Lin et al. ............ 424/78.03 |
| 6,291,372 | B1 | 9/2001 | Mumick et al. |
| 6,296,936 | B1 | 10/2001 | Yahiaoui et al. |
| 6,410,062 | B1 * | 6/2002 | Callaghan et al. ........ 424/764 |
| 6,436,234 | B1 | 8/2002 | Chen et al. |
| 6,530,910 | B1 | 3/2003 | Pomplun et al. |
| 6,537,663 | B1 | 3/2003 | Chang et al. |
| 6,548,592 | B1 | 4/2003 | Lang et al. |
| 6,579,570 | B1 | 6/2003 | Lang et al. |
| 6,599,848 | B1 | 7/2003 | Chen et al. |
| 6,602,955 | B2 | 8/2003 | Soerens et al. |
| 6,630,558 | B2 | 10/2003 | Chang et al. |
| 6,653,406 | B1 | 11/2003 | Soerens et al. |
| 6,670,521 | B2 | 12/2003 | Noda et al. |
| 6,683,143 | B1 | 1/2004 | Mumick et al. |
| 2001/0051796 | A1 | 12/2001 | Noda et al. |
| 2002/0081930 | A1 | 6/2002 | Jackson et al. |
| 2002/0091097 | A1 * | 7/2002 | Bratzler et al. ............ 514/44 |
| 2003/0008591 | A1 | 1/2003 | Parsons et al. |
| 2003/0022568 | A1 * | 1/2003 | Branham et al. .......... 442/59 |
| 2003/0027470 | A1 | 2/2003 | Chang et al. |
| 2003/0045191 | A1 | 3/2003 | Goldstein et al. |
| 2003/0045645 | A1 | 3/2003 | Chang et al. |
| 2003/0207772 | A1 | 11/2003 | Ahmad et al. |
| 2003/0211161 | A1 | 11/2003 | Ahmad et al. |
| 2003/0232090 | A1 | 12/2003 | Ahmad et al. |
| 2004/0138074 | A1 | 7/2004 | Ahmad et al. |
| 2004/0167039 | A1 | 8/2004 | Ahmad et al. |
| 2004/0185065 | A1 | 9/2004 | Ahmad et al. |
| 2006/0003654 | A1 * | 1/2006 | Lostocco et al. ........... 442/149 |

FOREIGN PATENT DOCUMENTS

| | | |
|---|---|---|
| EP | 0 021 693 A1 | 1/1981 |
| EP | 0 303 528 B1 | 2/1989 |
| EP | 0 608 460 A1 | 8/1994 |
| EP | 0 638 680 B1 | 2/1995 |
| EP | 0 792 144 B1 | 9/1997 |
| EP | 0 995 393 A2 | 4/2000 |
| EP | 1103250 A1 | 5/2001 |
| JP | 51-003248 A | 1/1976 |
| JP | 06-192527 A | 7/1994 |
| JP | 06-207162 A | 7/1994 |
| JP | 06-233809 A | 8/1994 |
| WO | WO 98/29461 A1 | 7/1998 |
| WO | WO 01/83573 A1 | 5/2001 |
| WO | 01/83573 | 11/2001 |
| WO | 1 285 985 A1 | 2/2003 |

OTHER PUBLICATIONS

Denton, Graham W., "Chlorhexidine," Chapter 16, *Disinfection, Sterilization, and Preservation*, Fourth Edition, edited by Seymour S. Block, published by Lea & Febiger, 1991, pp. 274-287.

Dychdala, G.R. and John A. Lopes, "Surface-Active Agents: Acid-Anionic Compounds," Chapter 14, *Disinfection, Sterilization, and Preservation*, Fourth Edition, edited by Seymour S. Block, published by Lea & Febiger, 1991, pp. 256-261.

Grulke, Eric A., "Solubility Parameter Values," Section VII: Solution Properties, *Polymer Handbook*, 4th Edition, 1999, pp. 675-714.

Kostenbauder, Harry B., "Physical Factors Influencing the Activity of Antimicrobial Agents," Chapter 4, *Disinfection, Sterilization, and Preservation*, Fourth Edition, edited by Seymour S. Block, published by Lea & Febiger, 1991, pp. 59-68.

Kunugi, S. et al., "Communications to the Editor: Effects of Pressure on the Behavior of the Thermoresponsive Polymer Poly(N-vinylisobutyramide) (PNVIBA)," *Macromolecules*, vol. 30, No. 15, 1997, pp. 4499-4501.

Larson, E.L. and H.E. Morton, "Alcohols," Chapter 11, *Disinfection, Sterilization, and Preservation*, Fourth Edition, edited by Seymour S. Block, published by Lea & Febiger, 1991, pp. 191-201.

Lee, Seungsin et al., "Antimicrobial and Blood Repellent Finishes for Cotton and Nonwoven Fabrics Based on Chitosan and Fluoropolymers," *Textile Research Journal*, 69(2), Feb. 1999, pp. 104-112.

Manning, A.J. and F. Rodriguez, "Predicting Solubilities of Vinyl Polymers," *Journal of Applied Polymer Science*, vol. 17, No. 6, John Wiley & Sons, Jun. 1973, pp. 1651-1662.

May, Oscar W., "Polymeric Antimicrobial Agents," Chapter 18, *Disinfection, Sterilization, and Preservation*, Fourth Edition, edited by Seymour S. Block, published by Lea & Febiger, 1991, pp. 322-332.

Merianos, John J., "Quaternary Ammonium Antimicrobial Compounds," Chapter 13, *Disinfection, Sterilization, and Preservation*, Fourth Edition, edited by Seymour S. Block, published by Lea & Febiger, 1991, pp. 225-252.

Rossmoore, H.W., "Nitrogen Compounds," Chapter 17, *Disinfection, Sterilization, and Preservation*, Fourth Edition, edited by Seymour S. Block, published by Lea & Febiger, 1991, pp. 290-317.

Russell, A.D., "Principles of Antimicrobial Activity," Chapter 3, *Disinfection, Sterilization, and Preservation*, Fourth Edition, edited by Seymour S. Block, published by Lea & Febiger, 1991, pp. 29-47.

Suwa, K. et al., "Effects of Salt on the Temperature and Pressure Responsive Properties of Poly(N-vinylisobutyramide) Aqueous Solutions," *Colloid Polymer Science*, vol. 276, Steinkopff Verlag, 1998, pp. 529-533.

Suwa, Kazuo et al., "Synthesis and Functionalities of Poly(N-vinylisobutyramide). IV. Synthesis and Free Radical Polymerization of N-vinylisobutyramide and Thermosensitive Properties of the Polymer," *Journal of Polymer Science: Part A: Polymer Chemistry*, vol. 35, John Wiley & Sons, Inc., 1997, pp. 1763-1768.

Suwa, Kazuo et al., "Synthesis and Functionalities of Poly(N-vinylisobutyramide). V. Control of a Lower Critical Solution Temperature of Poly(N-Vinylalkylamide)," *Journal of Polymer Science: Part A: Polymer Chemistry*, vol. 35, John Wiley & Sons, Inc., 1997, pp. 3087-3094.

Tiktopulo, Elizaveta I. et al., ""Domain" Coil—Globule Transition in Homopolymers," *Macromolecules*, vol. 28, No. 22, 1995, pp. 7519-7524.

McCormick, Charles, "Water-Soluble Polymers," Encyclopedia of Polymer Science and Technology, John Wiley & Sons, Inc., vol. 12, pp. 452-521.

"Water-Soluble Polymers," Encyclopedia of Polymer Science and Technology, John Wiley & Sons, Inc., vol. 12, p. 452, 489, 494.

Office action from U.S. Appl. No. 10/883,192, dated Mar. 17, 2009.

* cited by examiner

DISPERSIBLE ALCOHOL/CLEANING WIPES VIA TOPICAL OR WET-END APPLICATION OF ACRYLAMIDE OR VINYLAMIDE/AMINE POLYMERS

REFERENCE TO RELATED APPLICATION

This patent application is a continuation-in-part patent application of U.S. patent application Ser. No. 10/883,192 filed on Jun. 30, 2004.

BACKGROUND OF THE INVENTION

For many years, the problem of disposability has plagued industries that provide disposable products such as diapers, wet wipes, adult incontinent garments and feminine care products. While much headway has been made in addressing this problem, one of the weak links has been the inability to create an economical coherent fibrous web which will readily dissolve or disintegrate in water but still have sufficient in-use tensile strength.

Binder compositions have been developed which can be more dispersible and are more environmentally responsible than past binder compositions. One class of binder compositions includes polymeric materials having inverse solubility in water. These binder compositions are insoluble in warm water, but are soluble in cold water, such as found in a toilet. It is well known that a number of polymers exhibit cloud points or inverse solubility properties in aqueous media. These polymers include: (1) evaporation retarders; (2) temperature sensitive compositions, which are useful as temperature indicators due to a sharp color change associated with a corresponding temperature change; (3) heat sensitive materials that are opaque at a specific temperature and become transparent when cooled to below the specific temperature; (4) wound dressings with good absorbing characteristics and easy removal; and, (5) materials in flushable personal care products.

Other binders include a class of binders which are ion-sensitive. In some cases, terpolymers are used as binders for flushable nonwoven webs. The acrylic acid-based terpolymers, which comprise partially neutralized acrylic acid, butyl acrylate and 2-ethylhexyl acrylate, may be used as binders for use in flushable nonwoven webs in some parts of the world. However, because of the presence of a small amount of sodium acrylate in the partially neutralized terpolymer, such binders fail to disperse in water containing more than about 15 ppm $Ca^{2+}$ and/or $Mg^{2+}$. When placed in water containing more than about 15 ppm $Ca^{2+}$ and/or $Mg^{2+}$ ions, nonwoven webs using the above-described binders maintain a tensile strength greater than 30 g/in., which negatively affects the "dispersibility" of the nonwoven web. The proposed mechanism for the failure is that each calcium ion binds with two carboxylate groups either intramolecularly or intermolecularly. Intramolecular association causes the terpolymer chain to coil up, which eventually leads to polymer precipitation. Intermolecular association yields crosslinking. Whether intramolecular or intermolecular associations are taking place, the terpolymer is not soluble in water containing more than about 15 ppm $Ca^{2+}$ and/or $Mg^{2+}$. Due to the strong interaction between calcium ions and the carboxylate groups of the terpolymer, dissociation of the complex is highly unlikely because this association is irreversible. Therefore, the terpolymer that has been exposed to a high $Ca^{2+}$ and/or $Mg^{2+}$ concentration solution will not disperse in water even if the calcium concentration decreases. This limits the application of the terpolymer as a flushable binder material because most areas across the U.S. have hard water, which contains more than 15 ppm $Ca^{2+}$ and/or $Mg^{2+}$.

Other binders, while being in contact with an organic solvent, usually as a cleaning agent or a preservative, still require the presence of ions, such as monovalent or divalent metal ions, to establish sufficient stability during use and dispersibility at disposal. As discussed above, the issue of hard water may again apply to such binders.

In some dispersible cleaning or personal care products, such as a water-disintegratable cleansing sheet; i.e., wet wipe, comprising water-dispersible fibers treated with a water-soluble binder having a carboxyl group. The cleansing sheet is treated with a cleansing agent containing 5%-95% of a water-compatible organic solvent and 95%-5% water. The organic solvent is typically propylene glycol. The cleansing sheet retains wet strength and does not disperse in the organic solvent-based cleansing agent, but disperses in water. The cleansing sheets must have higher concentrations of organic solvents as these solvents ensure the in-use wet strength for the cleansing sheets. Without the solvents, the cleansing sheets would have little in-use wet strength and would not be effective as a wet wipe. However, the use of such high amounts of organic solvent results in a greasy after-feel when the cleansing sheet is used, and these organic solvents may cause discomfort and irritation to skin or mucosa in higher amounts.

The presence of harmful or unwanted microorganisms on the skin or mucosa can be a significant problem, resulting in discomfort or more serious health issues. By way of example, many women during their lives will suffer from a vaginal bacterial or fungal infection. These infections can occur for a variety of reasons. For example, the use of antibiotics may result in the overgrowth of *Candida albicans*, resulting in the condition known as vuvlovaginitis (vulvovaginal Candidiasis or VVC). This condition is typically treated by azole anti-fungal agents, applied intravaginally or orally. Some sufferers may believe their vaginal infection is a fungal infection when it is actually a bacterial infection. Common remedies for vaginal fungal infections are largely ineffective against vaginal bacterial infections, and the use of over-the-counter anti-fungal products may actually mask the bacterial infection. These bacterial infections are known as "bacterial vaginosis," and are much more common than VVC. Clinically, bacterial vaginosis is a polymicrobial vaginal infection caused by an increase in the number of anaerobic organisms with a concomitant decrease in the Lactobacilli in the vagina.

In normal conditions the predominant organism in the vagina, Lactobacilli, regulates the growth of anaerobes and other bacteria through the production of hydrogen peroxide and lactic acid from vaginal glycogen, in order to maintain vaginal acidity. It is, therefore, important that compositions and products intended for use on or around the vulvovaginal skin or mucosa do not adversely affect the population of Lactobacilli and that permit a healthy vaginal pH to be maintained.

Treatments for VVC and bacterial vaginosis known in the art generally relate to novel anti-fungal and anti-bacterial chemical compounds and penetration-enhancing formulations. Often these compounds involve the use of organic solvents, such as ethyl alcohol, in combination with other organic solvents to solubilize the anti-fungal and anti-bacterial compounds. However, these organic solvents can be irritating to the vulvovaginal skin or mucosa.

There are numerous personal cleansing products with a multitude of formulations and uses. However, when many personal hygiene products are contacted with the body, there is frequently a perception of cold. When an individual contacts the skin or mucosa with the product, the individual may experience an unpleasant or uncomfortable cold feeling due to the difference in temperature between the body and the ambient temperature of the product.

A variety of compositions are known in the art or described in the literature that claim to impart a warming sensation when applied to the skin or mucosa. Many of these compositions contain plant extracts or other compounds which are irritating to the skin or mucosa, and the associated feeling of warmth is by virtue of their irritant action. Other compositions claim to enhance blood flow in order to cause tissue warming. Still others purportedly work on the principle of freezing point depression, and rely on heating in the microwave or cooling in a refrigerator. Another cosmetic composition contains self-heating properties through a compound possessing a boron-oxygen-boron linkage, which reacts exothermically with water. However, none of these compositions combine a non-irritating, non-toxic warming composition with a disposable, dispersible cleaning or personal care product.

There exists a need for dispersible cleaning or personal care products possessing softness, flexibility, three dimensionality, and resiliency; wicking and structural integrity in the presence of aqueous or bodily fluids; and, true fiber dispersion after toilet flushing so that the cleaning or personal care product does not become entangled at obstructions, such as with tree roots or at bends in sewer pipes. Moreover, there is a need in the art for flushable cleaning or personal care products having water-dispersibility in all areas of the world, including soft and hard water areas. Furthermore, there is a need for water-dispersible binders that do not reduce wettability of the cleaning or personal care product with which they are used and are sprayable for relatively easy and uniform application to and penetration into the cleaning or personal care products. Finally, there is a need for water-dispersible, flushable wet wipes that are stable during storage and retain a desired level of wet strength during use when wetted with the appropriate cleaning, disinfection, or sanitizing wetting composition. Such a cleaning or personal care product is needed at a reasonable cost without compromising product safety and environmental concerns, something that past products have failed to do.

There is also a need for a cleaning or personal care product possessing the above properties that contains warming compositions which are non-toxic and non-irritating to impart a warming, soothing sensation, or increase blood circulation as a consequence of the warming, to the skin or mucosa when applied thereon.

Additionally, there is a need for a cleaning or personal care product that possesses the above properties that has the ability to act as a vehicle to deliver anti-microbial, pharmaceutical or treatment agents to the skin or mucosa when applied thereon.

SUMMARY OF THE INVENTION

The present invention is directed to triggerable binder formulations of acrylamide and vinylamide/amine polymers and polymer formulations, which have been developed to address the above-described problems. As used herein, the term "polymer" is understood to include polymers, copolymers, terpolymers, and higher order polymers. The triggerable binder formulations of the present invention may provide strength in the dry state, but more importantly, may help maintain a desired level of strength of the fibrous substrate in the wet state by solvent triggerability. A controlled concentration of an insolubilizing agent, such as a polyol or a lower level alcohol, glycol, ketone, or mixtures thereof, in the wetting composition insolubilizes the triggerable binder formulation and allows it to function as an adhesive for the fibers to form or further enhance a fibrous substrate. When the wet wipe is discarded into the wastewater stream, the insolubilizing agent concentration is diluted, the triggerable binder formulation becomes soluble, and the strength of the fibrous substrate drops below a critical level. The triggerable binder formulations of the present invention have a "trigger property," such that the triggerable binder formulations are insoluble in a wetting composition comprising an insolubilizing agent of a particular type and concentration, such as a polyol or a lower level alcohol, glycol, ketone, or mixtures thereof at concentrations above about 50% by weight, but are soluble when diluted with water, including hard water having 500 ppm (parts per million) or greater of calcium and magnesium ions. This allows the fibrous substrate to break apart into small pieces and, ultimately, disperse.

Unlike some ion-sensitive polymer formulations, which lose dispersibility in hard water because of ion cross-linking by calcium ions, the triggerable binder formulations of acrylamide and vinylamide/amine polymers and polymer formulations of the present invention are insensitive to calcium and/or magnesium ions at concentrations of a few hundred ppm and are insensitive to pH variations. Consequently, flushable cleaning or personal care products containing the triggerable binder formulations of the present invention maintain dispersibility of the fibrous substrates in hard water or soft water.

The polymers and polymer formulations of the present invention are useful as triggerable binder formulations and structural components for air-laid and wet-laid fibrous substrates, such as nonwoven fabrics, for applications, such as cleaning, hard surface cleaning, disinfecting, sanitizing, and personal care products. The polymers and polymer formulations of the present invention are particularly useful as triggerable binder formulations for flushable cleaning and personal care products, particularly wet wipes for personal use, such as cleaning or treating skin or mucosa, make-up removal, nail polish removal, medical care, and also wipes for use in hard surface cleaning, automotive care, including wipes comprising cleaning agents, disinfectants, and the like. The flushable cleaning or personal care products maintain integrity or wet strength during storage and use, and break apart or disperse after disposal in the toilet when the polyol or lower level alcohol concentration falls below a critical level. Suitable fibrous substrates for treatment with the triggerable binder formulations of the present invention include, but are not limited to tissue, such as creped or uncreped tissue, coform products, hydroentangled webs, air-laid mats, fluff pulp, nonwoven webs, and composites thereof. Methods for producing uncreped tissues and molded three-dimensional tissue webs of use in the present invention may be found in commonly owned U.S. Pat. No. 6,436,234, issued to Chen et al. on Aug. 20, 2002; U.S. Pat. No. 5,429,686, issued to Chiu et al. on Jul. 4, 1995; U.S. Pat. No. 5,399,412, issued to S. J. Sudall et al. on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; the disclosures of which are incorporated by reference to the extent they are non-contradictory herewith. The molded tissue structures of the above patents may be especially helpful in providing good cleaning in a wet wipe. Good cleaning may also be promoted by providing a degree of texture in the fibrous substrates as well by embossing, molding, wetting and through-air drying on a textured fabric, and the like. The acrylamide and vinylamide/amine polymers and polymer formulations of the present invention are particularly useful as triggerable binder formulations for fibrous substrates because the acrylamide and vinylamide/amine polymers and polymer formulations are substantive to the fibers.

Air-laid material may be formed by metering an airflow containing the fibers and other optional materials, in substantially dry condition, onto a typically horizontally moving wire forming screen. Suitable systems and apparatus for air-laying mixtures of fibers and thermoplastic material are disclosed in, for example, U.S. Pat. No. 4,157,724, issued to Persson on Jun. 12,1979 and reissued on Dec. 25, 1984 as Re. U.S. Pat. No. 31,775; U.S. Pat. No. 4,278,113, issued to Persson on Jul. 14, 1981; U.S. Pat. No. 4,264,289, issued to Day on Apr. 28, 1981; U.S. Pat. No. 4,352,649, issued to Jacobsen et al. on Oct. 5, 1982; U.S. Pat. No. 4,353,687, issued to Hosler, et al. on Oct. 12, 1982; U.S. Pat. No. 4,494,278, issued to Kroyer, et al. on Jan. 22, 1985; U.S. Pat. No. 4,627,806, issued to Johnson on Dec. 9, 1986; U.S. Pat. No. 4,650,409, issued to Nistri, et al. on Mar. 17, 1987; U.S. Pat. No. 4,724,980, issued to Farley on Feb. 16, 1988; and, U.S. Pat. No. 4,640,810, issued to Laursen et al. on Feb. 3,1987, the disclosures of which are incorporated by reference to the extent that they are non-contradictory herewith.

Coform is a nonwoven material comprising pulp or staple fibers and meltblown fibers. Coform products may be formed by impinging one or more streams of molten thermoplastic polymers onto an air-conveyed stream of pulp wood fibers. Modifications of this procedure are known in the art, such as by the inclusion of particulate material. Suitable systems and apparatus describing coform materials are disclosed in, for example, U.S. Pat. No. 6,296,936, assigned to Kimberly-Clark Worldwide.

The present invention also discloses how to make water-dispersible fibrous substrates, including wet wipes, which are stable in wetting compositions having an insolubilizing content, such as a polyol or a lower level alcohol, glycol, ketone, or mixtures thereof, using the above-described unique polymers and polymer formulations as triggerable binder compositions. The resultant treated fibrous substrates are flushable and water-dispersible due to the tailored sensitivity for insolubilizing agents, which can be triggered regardless of the hardness of water found in toilets throughout the United States and the world.

The present invention further discloses a suitable wetting composition for wet wipes. Wet wipes employing the polymers and polymer formulations as triggerable binder formulations of the present invention are stable during storage and retain a desired level of in-use tensile strength during use and are wetted with a wetting composition or cleaning agent comprising an insolubilizing agent, such as a polyol or a lower level alcohol, glycol, ketone, or mixtures thereof.

The present invention provides a dispersible, flushable wet wipe product comprising a fibrous substrate material, a triggerable binder formulation, and a wetting composition comprising an insolubilizing agent. The insolubilizing agent allows the wet wipe product to disperse in water when the insolubilizing agent concentration is diluted to a certain level. Specifically, the binder formulations include acrylamide and vinylamide/amine polymers or polymer formulations. The insolubilizing agent comprises one or more polyols, lower alcohols, lower glycols, lower ketones, and mixtures thereof. Other optional components suitable for use in the wetting composition include, for example, anti-microbial agents, pharmaceutical or treatment agents, and additional additives.

Briefly, therefore, the present invention is directed to a wet wipe product comprising a fibrous substrate material comprising fibers, a triggerable binder formulation for binding the fibers in the fibrous substrate material, and a wetting composition comprising an insolubilizing agent. The fibrous substrate material is wetted by the wetting composition, and the triggerable binder formulation is selected from the group consisting of acrylamide polymers and polymer formulations, vinyl/amine polymers and polymer formulations, and mixtures thereof. The triggerable binder formulation is insoluble in the wetting composition, and is dispersible in disposal water. The insolubilizing agent comprises one or more polyols, lower alcohols, lower glycols, lower ketones, or mixtures thereof.

The present invention is further directed to a wet wipe product comprising a fibrous substrate material comprising fibers, a triggerable binder formulation for binding the fibers in the fibrous substrate material, and a wetting composition comprising an insolubilizing agent comprising a polyol, wherein the wet wipe product delivers warming, soothing lubrication and moisturization to the skin or mucosa when applied thereon.

The present invention is further directed to a wet wipe product comprising a fibrous substrate material comprising fibers, a triggerable binder formulation for binding the fibers in the fibrous substrate material, and a wetting composition comprising an insolubilizing agent and at least one other additive, wherein the wet wipe product is a vehicle for delivering anti-microbial agents, pharmaceutical or treatment agents, or additional additives to the skin or mucosa when applied thereon.

The present invention is further directed to a method of making a wet wipe product comprising providing a fibrous substrate material, applying a triggerable binder formulation to the fibrous substrate material, drying the fibrous substrate material, and applying a wetting composition to the fibrous substrate material. The wetting composition comprises an insolubilizing agent comprising one or more polyols, lower alcohols, lower glycols, lower ketones, or mixtures thereof, and additionally optionally comprises anti-microbial agents, pharmaceutical or treatment agents, or additional additives.

The present invention is still further directed to a method of enhancing relaxation and/or increasing intimacy comprising wiping the skin or mucosa with a wet wipe product comprising a wetting composition comprising a polyol. Additionally, the present invention is directed to a method of treating female sexual dysfunction, and vuvlodynia, comprising wiping the skin or mucosa with a wet wipe product comprising a wetting composition comprising a polyol. Further, the present invention is directed to a method of treating or preventing bacterial vaginosis and/or vulvovaginal candidasis comprising wiping the skin or mucosa with a wet wipe product comprising a wetting composition further comprising an anti-microbial agent. The present invention is also directed to a method of treating or preventing Tinea cruris (jock-itch) and the like comprising wiping the skin or mucosa with a wet wipe product comprising a wetting composition further comprising an anti-microbial agent. Additionally, the present invention may be used to treat or prevent frostbite, hemorrhoids, and dental packings, and may also be used for cleaning oily or greasy surfaces.

These and other objects, features and advantages of the present invention will become apparent after a review of the following detailed description of the disclosed embodiments and the appended claims.

DETAILED DESCRIPTION OF THE DISCLOSED EMBODIMENTS

The present invention is practiced using triggerable binder formulations comprising acrylamide and vinylamide/amine polymers or polymer formulations. The triggerable binder formulations are an insolubilizing agent-sensitive acrylamide and vinylamide/amine polymer and polymer formulations. In order to be an effective insolubilizing agent-sensitive or triggerable polymer or polymer formulation for use in flushable or water-dispersible cleaning or personal care products, the triggerable binder formulations may be: (1) functional, i.e., maintain wet strength of the fibrous substrate under controlled conditions and dissolve or disperse in a reasonable period of time in soft or hard water, such as found in toilets and sinks around the world, thereby allowing the fibrous substrate dissolve or disperse; (2) safe (not toxic); and, (3) relatively economical. In addition to the foregoing factors, the insolubilizing agent-sensitive or triggerable binder formulations when used as a binder material for a fibrous substrate, such as a nonwoven fabric for use in a pre-moistened wipe or wet wipe (hereinafter referred to as wet wipe), may be: (4) processable on a commercial basis; i.e., may be applied relatively quickly on a large scale basis, such as by spraying, coating, printing, and the like; (5) provide acceptable levels of sheet or fibrous substrate wettability; (6) provide acceptable levels of sheet or fibrous substrate stiffness; and, (7) reduced tackiness of the fibrous substrate or the product that the fibrous substrate is incorporated into. The wetting composition with which the wet wipes of the present invention are treated may provide some of the foregoing advantages, and, in addition, may provide: (8) improved tactile properties; and, (9) cleaning, disinfecting, sanitizing properties. The insolubilizing agent-sensitive or triggerable binder formulations of the present invention and products made therewith, especially wet wipes comprising particular wetting compositions set forth below, may meet many or all of the above criteria. Of course, it is not necessary for all of the advantages of the embodiments of the present invention to be met to fall within the scope of the present invention.

Alcohol Triggerable Acrylamide And Vinylamide/amine Polymers and Polymer Formulations The insolubilizing agent-sensitive or triggerable binder formulations of the present invention comprise acrylamide and vinylamide/amine polymers and polymer formulations. The insolubilizing agent-sensitive or triggerable binder polymers may function as adhesives for tissue, air-laid pulp, wet-laid pulp, and other fibrous substrates and provide sufficient in-use tensile strength (typically about 300 g/in. or greater; about 500 g/in. or greater; or, about 1,000 g/in. or greater) when wetted with a wetting composition. The fibrous substrates may also be dispersible in tap water (including hard water up to 500 ppm or greater as metal ion), typically losing most of their in-use tensile strength between about 30 g/in. to about 75 g/in. in about 24 hours or less. Such insolubilizing agent-sensitive or triggerable binder formulations generally have the following structures:

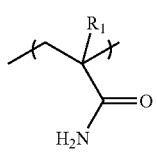

The $R_1$ moiety may be hydrogen or methyl.

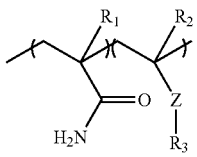

The $R_1$, and $R_2$ moieties may be independently hydrogen, methyl, or mixtures thereof. The Z moiety may be —O—, —COO—, —CONH—, —NHCO—, —NH$_2$, —NHR, and —NR$_2$. The $R_3$ moiety may be hydrogen, or any $C_1$ or higher alkyl group or aryl group, including methyl, ethyl, n-propyl, isopropyl, n-butyl, sec-butyl, tert-butyl, pentyl, hexyl, ethylhexyl, and the like.

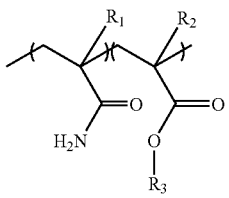

The $R_1$ and $R_2$ moieties may be independently hydrogen, methyl, or mixtures thereof. The $R_3$ moiety may be hydrogen, or any $C_1$ or higher alkyl group or aryl group, including methyl, ethyl, n-propyl, isopropyl, n-butyl, sec-butyl, tert-butyl, pentyl, hexyl, ethylhexyl, and the like.

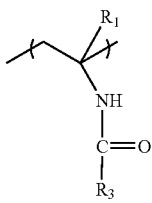

The $R_1$ moiety may be hydrogen or methyl. The $R_3$ moiety may be hydrogen, or any $C_1$ or higher alkyl group or aryl group, including methyl, ethyl, n-propyl, isopropyl, n-butyl, sec-butyl, tert-butyl, pentyl, hexyl, ethylhexyl, and the like.

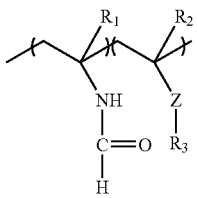

The $R_1$ and $R_2$ moieties may be independently hydrogen, methyl, or mixtures thereof. The Z moiety may be —O—, —COO—, —CONH—, —NHCO—, —NH$_2$, —NHR, and —NR$_2$. The $R_3$ moiety may be hydrogen, or any $C_1$ or higher alkyl group or aryl group, including methyl, ethyl, n-propyl, isopropyl, n-butyl, sec-butyl, tert-butyl, pentyl, hexyl, ethylhexyl, and the like.

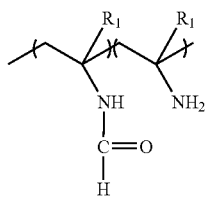

The $R_1$ moieties may be independently hydrogen, methyl, or mixtures thereof.

Polyacrylamide Polymers and Polymer Formulations

Polyacrylamide polymers and polymer formulations may be anionic, neutral, amphoteric, or positive in charge. Polymethacrylamide and other analogs may also be utilized. The presence of additional hydrophilic or charged groups may enhance solubility, dispersibility, and other properties of the polymers and polymer formulations.

Examples of anionic or acidic monomers that may be copolymerized into the backbone of the polymers and polymer formulations may include acrylic acid, methacrylic acid and their salts, 2-acrylamido-2-methyl-1 propanesulfonic acid (AMPS) and its salts, vinyl sulfonic acid and their salts, other sulfonate monomers such as potassium (3-sulfopropyl) acrylate, sodium styrene sulfonate, and phosphonate/phosphonic acids monomers. Useful neutral monomers include ones such as N-isopropyl acrylamide and other acrylamide derivatives, 2-hydroxyethyl methacrylate, vinyl pyrrolidone, methylvinyl ether, and polyethylene glycol (PEG) acrylate or methacrylates. Useful amphoteric or zwitterionic monomers include N, N-Dimethyl-N-(2-methacryloyloxyethyl)-N-(3-sulfopropyl) ammonium betaine, N,N-dimethyl-N-(2-methacrylamidopropyl)-N-(3-sulfopropyl) ammonium betaine, 1-(3-Sulfopropyl)-2-vinylpyridinium betaine, N-(3-carboxypropyl)-N-methacrylamido-ethyl-N,N-dimethyl ammonium betaine, and 4-vinylpiperidinium ethanecarboxy betaine. Useful cationic monomers include [2-(acryloxy)ethyl] trimethyl ammonium chloride (ADAMQUAT), [2-(methacryloxy)ethyl] trimethyl ammonium chloride (MADQUAT), (3-acrylamidopropyl) trimethyl ammonium chloride, N,N-diallyldimethyl ammonium chloride, [2-(acryloxy)ethyl] dimethylbenzyl ammonium chloride, [2-(methacryloxy)ethyl] dimethylbenzyl ammonium chloride, [2-(acryloxy)ethyl] dimethyl ammonium chloride, and [2-(methacryloxy)ethyl] dimethyl ammonium chloride. Precursor monomers such as vinylpyridine, dimethylaminoethyl acrylate, and dimethylaminoethyl methacrylate, which may be polymerized and quaternized through post-polymerization reactions may be used in the present invention. Monomers or quaternization reagents which provide different counter-ions such as bromide, iodide, or methyl sulfate are further alternatives applicable to the present invention. In some embodiments of the present invention, certain water-insoluble monomers may be used to lower the glass transition temperature (Tg) of the polyacrylamide polymers or polymer formulations or to provide other useful properties, wherein the insolubility in the presence of an insolubilizing agent is not compromised or solubility in water is not compromised. Such water-insoluble monomers may include lower level acrylates, such as methyl, ethyl or butyl acrylates, substituted acrylamides, alkyl vinyl ethers, or other vinyl monomers.

Preparation of Polyvinylamide/Amines Polymers and Polymer Formulations

Polyvinylamide/amine polymers or polymer formulations are typically produced by free radical polymerization of N-vinylamide monomers with degree of cationicity controlled by post-polymerization hydrolysis and pH. Such N-vinylamide monomers may include N-vinylformamide, N-vinylacetamide, and other N-vinyl alkylamides. Co-polymerization products of the N-vinylamide monomers with other monomers such as those described above may be useful in the present invention. One embodiment of the present invention may be the co-polymerization product of the N-vinylamide monomer with a vinyl ester monomer, such as vinyl acetate. Hydrolysis may yield co-polymers of vinylamide/amide monomers with vinyl alcohol monomers. The hydrolyzed polymer or polymer formulation may be highly reactive with a host of functional chemistries, resulting in the potential for unique combinations of properties in a water soluble polymer. Examples of said functional chemistries may include cyclic esters, epoxides, isocyanantes, carboxylates, organic (i.e., alkyl) halides, aldehydes, etc., wherein the insolubility in the presence of an insolubilizing agent is not compromised or solubility in water is not compromised.

Cyclic amide polymers or polymerformulations, such as polyvinylpyrrolidone and polyvinylcaprolactam, may also be useful in the present invention.

The acrylamide and vinylamide/amine polymers and polymer formulations of the triggerable binder formulations of the present invention may have an average molecular weight that varies depending on the ultimate use of the triggerable binder formulation. The triggerable binder formulation of the present invention may have a weight average molecular weight ranging from about 10,000 to about 1,000,000 grams per mol. More specifically, the triggerable binder formulations of the present invention may have a weight average molecular weight ranging from about 25,000 to about 500,000 grams per mole, or, more specifically still, from about 200,000 to about 400,000 grams per mole.

In one embodiment of the present invention, the above-described triggerable binder formulations may be used as binder materials for flushable and/or non-flushable cleaning or personal care products. In order to be effective as a binder material in flushable cleaning or personal care products throughout the United States, the triggerable binder formulations of the present invention may remain stable and maintain their integrity (in-use tensile strength) while dry or in relatively high concentrations of an insolubilizing agent, such as a polyol or lower level alcohols, lower level glycols, lower level ketones, and mixtures thereof, but become soluble in water when the concentration of the insolubilizing agent drops below about 50%. The triggerable binder formulations of the present invention may be insoluble in a solution containing at least about 50 weight percent of an insolubilizing agent, such as a polyol or a lower level alcohol, lower level glycol, lower level ketone, and mixtures thereof. More specifically, the triggerable binder formulations of the present invention may be insoluble in a solution containing from about 50% to about 100% by weight of an insolubilizing agent, such as a polyol or a lower level alcohol, a lower level glycol, a lower level ketone, and mixtures thereof. Even more specifically, the triggerable binder formulations of the present invention may be insoluble in a solution containing from about 65% to about 90% by weight of an insolubilizing agent, such as a polyol or a lower level alcohol, lower level glycol, ketone, and mixtures thereof. More specifically, the triggerable binder formulations of the present invention may be insoluble in a solution containing from about 70% to about 90% by weight of an insolubilizing agent, such as a polyol or a lower level alcohol, lower level glycol, lower level ketone, and mixtures thereof.

Suitable lower level alcohols, lower level glycols, lower level ketones, and mixtures thereof that may be utilized as insolubilizing agents, may include, but are not limited to: methyl alcohol; ethyl alcohol; n-propyl alcohol; isopropyl alcohol; n-butyl alcohol; sec-butyl alcohol; tert-butyl alcohol; ethylene glycol; 1,2 propandiol (propylene glycol); 1,3 propane diol; acetone; methylethyl ketone; and, mixtures thereof.

In one embodiment of the present invention, the insolubilizing agent comprises at least one polyol. Preferably, the polyol is a polyhydric alcohol, and more preferably, the insolubilizing agent comprises one or more polyhydric alcohols. Polyethylene glycol ethers may additionally be used, including polyethylene glycol ethers of propylene glycol, propylene glycol stearate, propylene glycol oleate, propylene glycol cocoate, and the like. By way of example, specific propylene glycol ethers include PEG-25 propylene glycol stearate, PEG-55 propylene glycol oleate, and the like. Where the insolubilizing agent comprises one or more polyhydric alcohols, the polyhydric alcohol is preferably a polyalkylene glycol and others selected from the group consisting of glycerol, diglycerol, polyglycerol, 1,3-butylene glycol, propylene glycol, dipropylene glycol, polypropylene glycol, hexylene glycol, polyethylene glycols of various molecular weights, trimethylene glycol, erythritol, pentaerythritol, sorbitan, glucose, sorbitol, malitol, sucrose, raffinose, trehalose, and mixtures thereof. More preferably, the insolubilizing agent is a propylene glycol, a polypropylene glycol, a polyethylene glycol, and mixtures thereof. Still more preferably, the polyethylene glycol may be selected from the group consisting of polyethylene glycol 300, polyethylene glycol 400, and mixtures thereof. Polypropylene glycols of various molecular weights may also be used. Further, PEGylated compounds such as peptide or protein derivatives obtained through PEGylation reactions may also be used, as well as block copolymers of polyethylene glycols, such as (ethylene glycol)-block-poly(propylene glycol)-block-(polyethylene glycol), poly-(ethylene glycol-ran-propylene glycol), and the like.

In one embodiment of the present invention, the wet wipe product wet with a wetting composition comprising an insolubilizing agent comprising one or more polyols is useful to deliver a warming, soothing feeling to the skin or mucosa when applied thereon. When the wet wipe is wiped on the skin or mucosa, some of the wetting composition on the wet wipe remains on those surfaces. The polyols increase in temperature upon exposure to moisture from the skin or mucosa, without causing irritation or harm thereon. The polyols additionally act as lubricating and/or moisturizing agents. The resulting warming, soothing lubrication and moisturization that results from contacting the skin or mucosa with the wetting composition may be used to enhance relaxation or increase intimacy for the user.

In another embodiment of the present invention, the resulting warmth that results upon contacting the skin or mucosa with the wetting composition is that the polyols therein may be used to enhance the absorption of additives in the wetting composition, such as anti-microbial agents, pharmaceutical or treatment agents, and additional additives. This may be done through the increase in wetting composition and skin or mucosal tissue temperature via the interaction between the polyols and the moisture on the skin or mucosa and subsequently released heat.

In still another embodiment of the present invention, the resulting warmth that occurs upon contacting the skin or mucosa with the wetting composition comprising one or more polyols may provide a method for treating ailments such as dysmenorrhea, menstrual cramping, or female sexual dysfunction, including such female sexual dysfunction disorders as female sexual arousal disorder, hypoactive sexual desire disorder, orgasmic disorder and the like. Additionally, the warmth may allow treatments of frost nip, frostbite, or accelerate the penetration of pharmacologically active materials into and through the skin or mucosa. Preferably, the wet wipe is applied to the skin or mucosa and some of the wetting composition comprising one or more polyols remains thereon. The resulting increase in temperature serves to increase blood flow to those areas, and the increased blood flow acts as a treatment for these ailments.

In some embodiments of the present invention where the objective of the cleaning or personal care product is to provide disinfecting, sanitizing, or sterilizing properties, it may be undesirable to use a neat solvent wetting solution. It is known that the inclusion of water may enhance the disinfecting, sanitizing, or sterilizing properties of the wetting solution. Alcohols disinfect, sanitize, or sterilize primarily through denaturation (precipitation) of proteins that make up the cell wall of bacteria and other microorganisms. This denaturing effect may be less effective in the absence of water.

Additional insolubilizing agents useful in the present invention may include water-immiscible solvents. Hydrocarbons, such as $C_6$ and higher alkanes, including hexanes and octanes, toluenes, xylene, methylene chloride, and chloroform may be useful as insolublizing agents in wetting compositions.

Triggerable Binder Formulations and Fibrous Substrates Containing the Same

The triggerable binder formulations of acrylamide and vinylamide/amine polymers and polymer formulations of the present invention may be used as binders. The triggerable binder formulations of the present invention may be applied to any fibrous substrate. The triggerable binder formulations are particularly suitable for use in water-dispersible cleaning or personal care products. Suitable fibrous substrates include, but are not limited to, nonwoven and woven fabrics. In many embodiments, particularly cleaning or personal care products, fibrous substrates may be nonwoven fabrics. As used herein, the term "nonwoven fabric" refers to a fibrous substrate that has a structure of individual fibers or filaments randomly arranged in a mat-like fashion (including papers). Nonwoven fabrics may be made from a variety of processes including, but not limited to, air-laid processes, wet-laid processes, hydroentangling processes, staple fiber carding and bonding, solution spinning, and any other method known to one skilled in the art.

The triggerable binder formulation may be applied to the fibrous substrate by any known process of application. Suitable processes for applying the triggerable binder formulation include, but are not limited to, printing, spraying, electrostatic spraying, coating, flooded nips, metered press rolls, impregnating or by any other technique. The amount of the triggerable binder formulation may be metered and distributed uniformly within the fibrous substrate or may be non-uniformly distributed within the fibrous substrate. The triggerable binder formulation may be distributed throughout the entire fibrous substrate or it may be distributed within a multiplicity of small closely spaced areas. Alternatively, the formulation may be applied in various patterns, such as in well defined straight lines, wavy lines, or sloppy patterns. The triggerable binder formulation may be applied to the fibers prior to incorporation of the fibers into a fibrous substrate.

The solution of the triggerable binder formulation may contain up to about 50 percent by weight of triggerable binder formulation solids. More specifically, the solution of the triggerable binder formulation may contain from about 2 to about 20 percent by weight of triggerable binder formulation solids, more specifically about 5 to about 10 percent by weight of triggerable binder formulation solids. Plasticizers, perfumes, coloring agents, antifoams, bactericides, preservatives, surface active agents, thickening agents, fillers, opacifiers, tackifiers, detackifiers, co-binder polymers, and similar additives may be incorporated into the solution of the triggerable binder formulation, if so desired.

Once the triggerable binder formulation is applied to the fibrous substrate, the fibrous substrate may be dried by any conventional means. Once dry, the coherent fibrous substrate exhibits improved in-use tensile strength when compared to the in-use tensile strength of the untreated wet-laid or air-laid fibrous substrates, and yet has the ability to rapidly "fall apart", or disintegrate when placed in soft or hard water having a divalent ion concentration of about 500 ppm or greater of $Ca^{2+}$ and/or $Mg^{2+}$, and agitated. For example, the dry tensile strength of the triggerable binder formulation treated fibrous substrate may be increased by at least about 25 percent as compared to the dry tensile strength of the untreated fibrous substrate. More particularly, the dry tensile strength of the triggerable binder formulation treated fibrous substrate may be increase by at least about 100 percent as compared to the dry tensile strength of the untreated fibrous substrate. Even more particularly, the dry tensile strength of the fibrous substrate treated with the triggerable binder formulation may be increased by at least about 500 percent as compared to the dry tensile strength of the untreated fibrous substrate.

One feature of the present invention is that the improvement in the in-use tensile strength is effected where the amount of triggerable binder formulation present, "add-on", in the resultant fibrous substrate may represent only a small portion by weight of the entire fibrous substrate. The add-on level of the triggerable binder formulation may depend upon the in-use tensile strength is that is desired in the fibrous substrate and the product into which the fibrous substrate is incorporated. Typically, dense, low caliper fibrous substrates may require a lower add-on level of the triggerable binder formulation to obtain targeted properties while lofty, higher caliper fibrous substrates may require a higher add-on level of the triggerable binder formulation to obtain targeted properties. In addition, wet-laid fibrous substrates may require a lower add-on level of the triggerable binder formulation in the presence of an inherent dry strength resulting from fiber-fiber hydrogen bonding. Air-laid fibrous substrates may require a higher add-on level of the triggerable binder formulation because such fibrous substrates typically lack an inherent dry strength because hydrogen bonding is less likely to be present within the fibrous substrate.

The amount of "add-on" may vary for a particular application; however, the optimum amount of "add-on" results in a fibrous substrate which has integrity (desired in-use tensile strength) while in use and also quickly disperses, referred to herein as disposal strength, (typically about 75 g/in. or less; about 50 g/in. or less; or, about 20 g/in. or less) when soaked in water. Typically a lower add-on level is required for wet-end application than for a topical application. For example, the topical add-on level of the triggerable binder formulations may range from about 0.5% to about 25%, by weight, of the total dry fiber weight of the fibrous substrate. More particularly, the topical add-on level of the triggerable binder formulation may range from about 2% to about 15%, by weight, of the total dry fiber weight of the fibrous substrate. Even more particularly, the topical add-on level of the triggerable binder formulations may be from about 5% to about 12% by weight of the total dry fiber weight of the fibrous substrate. For wet-end application, the wet-end add-on level of the triggerable binder formulations may range from about 0.1% to about 2%, by weight, of the total dry fiber weight of the fibrous substrate. More particularly, the wet-end add-on level of the triggerable binder formulation may range from about 0.3% to about 1%, by weight, of the total dry fiber weight of the fibrous substrate. Even more particularly, the wet-end add-on level of the triggerable binder formulations may be from about 0.5% to about 1% by weight of the total dry fiber weight of the fibrous substrate.

The treated fibrous substrates of the present invention may have good in-use tensile strength, as well as, triggerability based on the presence of an insolubilizing agent. The fibrous substrates treated with the triggerable binder formulation of the present invention may be abrasion resistant and retain significant tensile strength in aqueous wetting compositions containing the specific amount and type of the insolubilizing agent, such as a polyol or lower level alcohols, glycols, ketones, and mixtures thereof, disclosed herein.

The fibers forming the fibrous substrates may be made from a variety of materials including natural fibers, synthetic fibers, and combinations thereof. The choice of fibers depends upon, for example, the intended end use of the finished fibrous substrate, such as a nonwoven fabric, and fiber cost. For instance, the fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise be used. Blends of one or more of the above fibers may also be used, if so desired. Among the wood pulp fibers, any known papermaking pulp fibers may be used, including softwood and hardwood pulp fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lenzig Lyocell® (available from Lenzig AG, with offices in Mobile, Ala.). Chemically treated natural cellulosic fibers may be used, such as mercerized pulps, chemically stiffened or crosslinked fibers, or sulfonated fibers. Recycled fibers, as well as virgin fibers, may be used. Cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermo-mechanical wood pulp, chemical wood pulp, debonded chemical wood pulp, milkweed, and bacterial cellulose.

The triggerable binder formulation of the present invention may also be applied to other fibers or particles. Other fibers that may be treated with the triggerable binder formulation of the present invention may include fibers such as those made fibers made from carboxymethyl cellulose, chitin, and chitosan. The triggerable binder formulation of the present invention may also be applied to particles, such as sodium polyacrylate superabsorbent particles. Superabsorbent particles are frequently incorporated on or into fibrous substrates used for cleaning or personal care products, especially nonwoven fabrics.

The fiber length is important in producing the fibrous substrates, such as nonwoven fabrics, of the present invention. The minimum length of the fibers depends on the method selected for forming the fibrous substrate. For example, where the fibrous substrate is formed by carding, the length of the fiber should usually be at least about 42 mm in order to insure uniformity.

Where the fibrous substrate is formed by air-laid or wet-laid processes, the fiber length may desirably be about 0.2 mm to about 6 mm. Although fibers having a length of greater than 50 mm may be used, it has been determined that when a substantial quantity of fibers having a length greater than about 15 mm is placed in a flushable fabric, though the fibers will disperse and separate in water, their length tends to form "ropes" of fibers, which are undesirable when flushing in home toilets. Therefore, for these products, it is desired that the fiber length be about 15 mm or less so that the fibers will not have a tendency to "rope" when they are flushed through a toilet. Although fibers of various lengths are applicable in the present invention, desirably fibers are of a length less than about 15 mm so that the fibers disperse easily from one another when in contact with water. The fibers, particularly synthetic fibers, may also be crimped.

The fibrous substrates, such as woven and nonwoven fabrics, may be formed from a single layer or multiple layers. In the case of multiple layers, the layers are generally positioned in a juxtaposed or surface-to-surface relationship and all or a portion of the layers may be bound to adjacent layers. The fibrous substrates may also be formed from a plurality of separate webs wherein the separate webs may be formed from single or multiple layers. In embodiments of the present invention where the fibrous substrate includes multiple layers, the entire thickness of the fibrous substrate may be subjected to an application of the triggerable binder formulation or each individual layer may be separately subjected to an application of the triggerable binder formulation and then combined with other layers in a juxtaposed relationship to form the finished fibrous substrate, such as woven or nonwoven fabrics.

In one embodiment of the present invention, the fibrous substrates may be incorporated into cleaning products, such as wet wipes, cleaning wipes for cleansing hard surfaces, and the like. These products may comprise one or more layers of a fluid-pervious element, such as fibrous tissue, gauze, plastic netting, etc.

The triggerable binder formulations of the present invention may be useful for binding fibers of air-laid or wet-laid fibrous substrates, such as nonwoven fabrics. The basis weights for air-laid or wet-laid fibrous substrates may range from about 10 grams per square meter ("gsm") to about 200 gsm. More specifically, the basis weights for the fibrous substrates may range from about 20 gsm to about 70 gsm and more specifically, from about 30 gsm to about 70 gsm. The basis weight, caliper, and other properties may be chosen to deliver desired attributes such as bulk, stretch, resiliency, toughness, and the like. The air-laid fibrous substrates may be especially useful for a wet wipe. The basis weights for such air-laid fibrous substrates may range from about 20 gsm to about 200 gsm with staple fibers having a denier of about 0.5 to about 10 and a length of about 6 to about 15 millimeters.

The fibrous substrates may also be incorporated into such body fluid absorbing products as pads, surgical dressings, tissues and the like. The triggerable binder formulation is such that it will not dissolve when contacted by body fluids. The fibrous substrate retains its structure, softness and exhibits a toughness satisfactory for practical use. However, when the fibrous substrate is brought into contact with water having a concentration of an insolubilizing agent, such as a polyol or a lower level alcohol, lower level glycol, lower level ketone, or mixtures thereof, up to about 300 ppm or less, the triggerable binder formulation disperses. The fibrous substrate is then easily broken and dispersed or dissolved in the water.

In one embodiment of the present invention, the in-use tensile strength of a fibrous substrate may be enhanced by forming the fibrous substrate with a binder material comprising the triggerable binder formulation of the present invention and subsequently applying an insolubilizing agent, such as a polyol or a lower level alcohol, glycol, ketone, or mixtures thereof, to the fibrous substrate. The insolubilizing agent may be applied to the fibrous substrate by any method known to those of ordinary skill in the art including spraying a solution onto the fibrous substrate. The amount of the insolubilizing agent may vary depending on a particular application. However, the amount of the insolubilizing agent may be applied to the fibrous substrate may be from about 50 weight percent to about 700 weight percent of the insolubilizing agent based on the total weight of the fibrous substrate. The insolubilizing agent-containing fibrous substrates of the present invention may be used in a variety of fibrous substrates applications including, but not limited to, wipe products, such as wet wipes, cleaning wipes for hard surfaces, and the like.

Those skilled in the art will readily understand that the triggerable binder formulations and fibrous substrates of the present invention may be advantageously employed in the preparation of a wide variety of products, including but not limited to, cleaning or personal care products designed to be contacted with body fluids. Such cleaning or personal care products may only comprise a single layer of the fibrous substrate, or may comprise a combination of elements, as described above. Although the triggerable binder formulations and fibrous substrates of the present invention are particularly suited for cleaning or personal care products, the triggerable binder formulations and fibrous substrates may be advantageously employed in a wide variety of consumer products.

The triggerable binder formulations of the present invention may be activated as binders without the need for elevated temperature. While drying or water removal may be useful in achieving a good distribution of the triggerable binder formulation in a fibrous substrate, elevated temperature, per se, is not essential because the triggerable binder formulation does not require crosslinking or other chemical reactions with high activation energy to serve as a binder within the fibrous substrate. Rather, the interaction with a soluble insolubilizing agent, typically a polyol or a lower level alcohol, glycol, ketone, or mixtures thereof, is sufficient to cause the triggerable binder formulation to become insoluble; i.e., activated by interaction between the insolubilizing agent and the triggerable binder formulation. Thus, a drying step may be avoided, if desired, or replaced with low-temperature water removal operations such as room-temperature drying or freeze drying. Elevated temperature is generally helpful for drying, but the drying may be done at temperatures below what is normally needed to drive crosslinking reactions. Thus, the peak temperature to which the fibrous substrate is exposed or to which the fibrous substrate is brought may be below any of the following: 200° C., 180° C., 160° C., 140° C., 120° C., 110° C., 105° C., 100° C., 90° C., 75° C., and 60° C.

Wet Wipe Wetting Composition and Wet Wipes Containing the Same

One embodiment of the present invention is the production of wet wipes comprising the triggerable binder formulations and fibrous substrates. For wet wipes, the fibrous substrate may be in the form of a woven or nonwoven fabric; however, nonwoven fabrics may be more typical. The fibrous substrate may be formed from relatively short fibers, such as wood pulp fibers. The minimum length of the fibers may depend on the method selected for forming the fibrous substrate, such as a nonwoven fabric. Where the fibrous substrate is formed by a wet or dry method, the fiber length may range from about 0.1 millimeters to 15 millimeters. The fibrous substrate for use in the present invention may have a relatively low wet cohesive strength when it is not bonded together by an adhesive or binder material. When such fibrous substrates are bonded together by a triggerable binder formulation, which loses its bonding strength in tap water and in sewer water, the fibrous substrate may break up readily by the agitation provided by flushing and moving through the sewer pipes.

The finished wet wipes may be individually packaged, desirably in a folded condition, in a moisture and/or solvent proof envelope or packaged in containers holding any desired number of sheets of wet wipes in a moisture/solvent-tight package with a wetting composition applied to the wet wipe. The finished wet wipes may also be packaged as a roll of separable sheets of wet wipes in a moisture/solvent-proof container holding any desired number of sheets of wet wipes on the roll with a wetting composition applied to the wet wipes. The roll may be coreless and either hollow or solid. Coreless rolls, including rolls with a hollow center or without a solid center, may be produced with known coreless roll winders, including those of SRP Industry, Inc. located in San Jose, Calif.; Shimizu Manufacturing located in Japan; and, the devices discussed in U.S. Pat. No. 4,667,890, issued to Gietman on May 26, 1987. Solid-wound coreless rolls may offer more product for a given volume and may be adapted for a wide variety of dispensers.

Relative to the weight of the dry fibrous substrate, the wet wipe may contain from about 10 percent to about 500 percent of the wetting composition, more specifically from about 100 percent to about 400 percent of the wetting composition, and even more specifically from about 200 percent to about 300 percent of the wetting composition. The wet wipe may maintain its desired characteristics over the time periods involved in warehousing, transportation, retail display and storage by the consumer.

Various forms of impermeable envelopes and storage means for containing wet-packaged materials, such as wipes and towelettes and the like, are well known in the art. Any of these may be employed in packaging the wet wipes of the present invention.

The wet wipes of the present invention are wetted with an solvent-based wetting composition, which has one or more of the following properties:

(1) is compatible with the above-described triggerable binder formulations of the present invention;

(2) enables the pre-moistened wipe to maintain its wet strength during converting, storage and usage (including dispensing), as well as, dispersibility in a toilet bowl;

(3) reduces tackiness of the wipe, and provides tactile properties, such as skin glide and a "lotion-like feel";

(4) acts as a vehicle to deliver cleansing, sanitizing, or disinfecting benefits;

(5) acts as a vehicle to deliver "moist cleansing" and other skin health benefits; and, (6) provides for rapid evaporation and/or drying.

In one aspect of the present invention, the wetting composition may contain an insolubilizing agent that maintains the strength of a water-dispersible triggerable binder formulation until the insolubilizing agent is diluted with water, whereupon the strength of the water-dispersible triggerable binder formulation begins to decay. The water-dispersible triggerable binder formulation may be any of the triggerable binder formulations of the present invention. The insolubilizing agent in the wetting composition may be a polyol or a lower level alcohol, glycol, ketone, or mixtures thereof which provides in-use and storage strength to the water-dispersible triggerable binder formulation, and may be diluted in water to permit dispersion of the fibrous substrate as the triggerable binder formulation triggers to a weaker state. Examples of lower level alcohols, glycols, and ketones may include, but are not limited to: methyl alcohol; ethyl alcohol; n-propyl alcohol; isopropyl alcohol; n-butyl alcohol; sec-butyl alcohol; tert-butyl alcohol; ethylene glycol; 1,2 propandiol (propylene glycol); 1,3 propane diol; acetone; methylethyl ketone; and, mixtures thereof.

In one embodiment of the present invention, the insolubilizing agent comprises at least one polyol. Preferably, the polyol is a polyhydric alcohol, and more preferably, the insolubilizing agent comprises one or more polyhydric alcohols. Polyethylene glycol ethers may additionally be used, including polyethylene glycol ethers of propylene glycol, propylene glycol stearate, propylene glycol oleate, propylene glycol cocoate, and the like. By way of example, specific propylene glycol ethers include PEG-25 propylene glycol stearate, PEG-55 propylene glycol oleate, and the like. Where the insolubilizing agent comprises one or more polyhydric alcohols, the polyhydric alcohol is preferably a polyalkylene glycol and others selected from the group consisting of glycerol, diglycerol, polyglycerol, 1,3-butylene glycol, propylene glycol, dipropylene glycol, polypropylene glycol, hexylene glycol, polyethylene glycols of various molecular weights, trimethylene glycol, erythritol, pentaerythritol, sorbitan, glucose, sorbitol, malitol, sucrose, raffinose, trehalose, and mixtures thereof. More preferably, the insolubilizing agent is a propylene glycol, a polypropylene glycol, a polyethylene glycol, and mixtures thereof. Still more preferably, the polyethylene glycol may be selected from the group consisting of polyethylene glycol 300, polyethylene glycol 400, and mixtures thereof. Polypropylene glycols of various molecular weights may also be used. Further, PEGylated compounds such as peptide or protein derivatives obtained through PEGylation reactions may also be used, as well as block copolymers of polyethylene glycols, such as (ethylene glycol)-block-poly(propylene glycol)-block-(polyethylene glycol), poly-(ethylene glycol-ran-propylene glycol), and the like.

Determination of a suitable lower level alcohol, glycol, ketone, or mixtures thereof may be conducted using the solubility. The solubility of an amorphous polymer in a given solvent is governed by the Gibbs free energy of mixing given by Equation (1):

$$\Delta G_m = \Delta H_m - T \Delta S_m \qquad (1)$$

$\Delta G_m$ is the free energy change of the system upon mixing. $\Delta H_m$ and $\Delta S_m$ are the enthalpy and entropy change upon mixing, respectively, and T is the absolute temperature. When the free energy of mixing is less than zero ($\Delta G_m < 0$) for a given polymer and solvent (or solvent mixture thereof), a single-phase system is obtained and mixing occurs spontaneously. Since dissolution of a high molecular weight polymer is almost always accompanied by an increase in entropy of the system ($\Delta S_m > 0$), the sign and magnitude of $\Delta H_m$ is generally the deciding factor for solubility.

Solubility parameters, originally developed to describe enthalpy of mixing with simple nonpolar solvents, have been extended to describe the interactions of polymers and polar solvent. The enthalpy of mixing of such systems is expressed in a form like Equation (2):

$$\Delta H_m = V\left[\left(\frac{\Delta E_1^v}{V_1}\right)^{1/2} - \left(\frac{\Delta E_2^v}{V_2}\right)^{1/2}\right]^2 \phi_1 \phi_2 \quad (2)$$

V is the volume of the mixture, $\Delta E_1^V$ is the ideal energy of vaporization of the solvent, and $\Delta E_2^V$ is the ideal or theoretical energy of vaporization of the polymer. $V_1$ and $V_2$ are the partial molar volumes of the solvent and polymer, respectively. $\phi_1$ and $\phi_2$ are the respective volume fractions. The ($\Delta E_i^V/V_i$) terms represent "cohesive energy density" values and correspond to the energy of vaporization per unit volume of a component under ideal conditions. The solubility parameter or Hildebrand parameter, $\delta$, is defined as the square root of the cohesive energy density, given by Equation (3):

$$\delta_i = \left(\frac{\Delta E_i^v}{V_i}\right)^{1/2} \quad (3)$$

The solubility parameter describes the attractive strength between the molecules of a material and is sometimes referred to as an "internal cohesion parameter". For the mixing of two substances to take place, the breaking of these internal cohesive forces must occur.

Substituting the results from Equation (3) and Equation (2) into Equation (1) and canceling the bulk volume term (V) yields the following result, where $v_1$ and $v_2$ are the relative volumes of the solvent and polymer, respectively, as depicted in Equation (4):

$$\Delta G_m = ((\delta_1 - \delta_2)^2 v_1 v_2) - T\Delta S_m \quad (4)$$

Equation (4) represents the thermodynamic basis for the old chemical rule-of-thumb, "like dissolves like". When $\delta_1 = \delta_2$, the enthalpic term goes to zero and the free energy of mixing is always negative. If the difference is small, the entropic term may out weight the enthalpy and spontaneous mixing will still occur. If the difference in $\delta$ values is large, then the magnitude of the enthalpic term will out-weigh the entropy gain and mixing will not occur. In such cases where the difference in solubility parameters for a polymer-solvent combination is large, the solvent is considered to be a "non-solvent" for the polymer.

The units of $\delta$ may be difficult to rationalize. They are generally expressed as units of MPa½ or (cal/cm³)$^{1/2}$. One simple way to understand these units is to note that Equation (4) calls for a solution in terms of a quantity of energy. It can be readily seen that substitution of $\delta$ values in terms of (cal/cm³)$^{1/2}$ or MPa½ into Equation (4) results in a quantity of energy in terms of calories or joules, respectively, after unit cancellation (1 MPa=1 kJ/m³). For purposes of the present work, (cal/cm³)$^{1/2}$ units for $\delta$ will be used.

Finally, in the extension of solubility parameters to polar systems, one should recognize the presence and activity of hydrogen bonding. Hydrogen bonding forces may be much stronger than van der Waals and dipole forces and may dominate the enthalpy of mixing. In general, complete miscibility may be only expected when the solubility parameter and hydrogen bonding character are similar. The contribution of hydrogen bonding applies to the solubility of polar vinyl polymers, such a polyacrylamide and polyvinyl pyrrolidone. In this study, numerical hydrogen bonding indices are assigned. Often, however, solvents are assigned to a hydrogen-bonding group: strong (s); moderate (m); and, poor (p). Direct comparison of physical properties of polymer-solvent pairs based on $\delta$ values will usually be done within the same hydrogen bonding group.

A vast number of solvent solubility parameter values are available in the *Polymer Handbook*, 4$^{th}$ Edition, John Wiley & Sons, New York, (1999), the disclosure of which is incorporated by reference to the extent it is non-contradictory herewith. Table A shows the solubility parameters and hydrogen bonding groups for selected solvents. Note that all the solvents selected are strong hydrogen bonders except for acetone, which has moderate hydrogen bonding ability. Typically, miscibility with water is desirable for disposal in common waste-water streams, but other solvents may also be suitable. $\delta$ values for these solvents range from 14.5 to 9.9. Water, on the other hand, has a much higher value of 23.4, is a strong hydrogen bonder, and is known to be a very good solvent for many polymers with polar groups, hence the term "water-soluble polymers".

A $\delta$ value for polyacrylamide homopolymer (PAM) of 21 (cal/cm³)$^{1/2}$ has been assigned for comparison. This also allows calculation of the cohesive energy difference parameter, $(\delta_1 - \delta_2)^2$, for each solvent with PAM. These data are also presented in Table A. A solubility parameter is not readily available for polyvinylamine/vinylamide resins. However, polyvinylformamide is a structural isomer and should be expected to have similar values through functional group contributions. Therefore, copolymers derived from this material should have similar solubility behavior as acrylamide copolymers and some license may be taken in discussing their behavior generically as "polyacrylamide", unless specific differences are being highlighted.

With decreasing $\delta$ value or increasing cohesive energy difference, the solvents in Table A should become better non-solvents for polyacrylamide. Therefore, fibrous substrates treated with polyacrylamide and wetted with non-solvent should show high in-use strength. Strength should somehow correlate with the non-solvency of the wetting fluid or $\delta$ value. In certain cases, it may be desirable to use a mixture of one or more of the solvents with water. In these cases, solvency (or non-solvency) of the solvent mixture may be evaluated by calculating a weighted average or "apparent" solubility parameter ($\delta_{1(app)}$) and properties of the fibrous substrate should governed by the relative amounts of solvent and non-solvent in the solvent mixture.

TABLE A

Solubility parameter values and hydrogen bonding groups for selected solvents.

| Solvent | ID | Solubility Parameter, $\delta$ (cal/cm³)$^{1/2}$ | $(\delta_1 - \delta_2)^2$ PAM | H-Bonding Group |
|---|---|---|---|---|
| Water | $H_2O$ | 23.4 | 5.8 | s |
| Methyl alcohol | MeOH | 14.5 | 42.3 | s |
| Ethyl alcohol | EtOH | 12.7 | 68.9 | s |
| Propylene glycol | PPG | 12.6 | 70.6 | s |
| n-Propyl alcohol | NPA | 11.9 | 82.8 | s |

TABLE A-continued

Solubility parameter values and hydrogen bonding groups for selected solvents.

| Solvent | ID | Solubility Parameter, δ (cal/cm$^3$)$^{1/2}$ | $(\tilde{\delta}_1 - \delta_2)^2$ PAM | H-Bonding Group |
|---|---|---|---|---|
| Isopropyl alcohol | IPA | 11.5 | 90.3 | s |
| n-Butyl alcohol | NBA | 11.4 | 92.6 | s |
| t-Butyl alcohol | TBA | 10.6 | 108.2 | s |
| Acetone | ACE | 9.9 | 123.2 | m |

The wetting composition may contain more than about 30 weight percent of the insolubilizing agent based on the total weight of the wetting composition for triggerable binder polymers or polymer formulations. Specifically, the wetting composition may contain from about 50 weight percent to about 100 weight percent of the insolubilizing agent. Even more specifically, the wetting composition may contain from about 65 weight percent to about 90 weight percent of an insolubilizing agent. More precisely, the wetting composition may contain from about 70 weight percent to about 90 weight percent of the insolubilizing agent.

The wetting composition of the present invention may further comprise a variety of additives compatible with the insolubilizing agent and the water-dispersible triggerable binder formulation, such that the strength and dispersibility functions of the wet wipe are not jeopardized. Suitable additives in the wetting composition include, but are not limited to, the following additives: chelators; odor control agents; detackifying agents to reduce the tackiness of the triggerable binder formulation; particulates; antimicrobial agents; preservatives; wetting agents and cleaning agents, such as detergents, surfactants, and some silicones; emollients; humectants; surface feel modifiers for improved tactile sensation (e.g., lubricity) on the skin; fragrance; fragrance solubilizers; opacifiers; fluorescent whitening agents; stabilizers; oxidizers; UV absorbers; pharmaceuticals; and, pH control agents, such as malic acid and potassium hydroxide.

Examples of wetting compositions are described in U.S. Pat. No. 5,145,663, issued to Simmons on Sep. 8, 1992 and U.S. Pat. No. 5,441,723, issued to Simmons on Aug. 15, 1995, the disclosures of which are incorporated by reference to the extent that they are non-contradictory herewith.

Anti-Microbial, Pharmaceutical or Treatment Additives

In order to better enhance the benefits to consumers, anti-microbial, and pharmaceutical or treatment agents may additionally be incorporated into the wetting composition described herein without jeopardizing the strength and dispersibility functions of the wet wipe of the present invention. The wet wipe of the present invention acts as a vehicle to deliver these anti-microbial or pharmaceutical or treatment agents to the skin or mucosa when applied thereon. Where the wetting composition comprises one or more polyols, the polyols therein may be used to enhance the absorption of additives in the wetting composition through the skin or mucosal tissue when applied thereon.

Anti-Microbial Agents

The wetting composition preferably contains one or more anti-microbial agents which advantageously destroy or prevent the growth of undesirable microbials on the skin or mucosa when the wet wipe of the present invention is wiped thereon. The wet wipes of the present invention can be used for any type of personal cleansing, and the addition of an anti-microbial agent assists in the removal or destruction of unwanted microorganisms from the skin or mucosa. Preferably, these anti-microbial agents destroy or otherwise regulate the amount harmful microbes, such as Escherichia coli, Candida albicans, or Staphylococcus aureus, on the body, but do not affect the body's natural microbial homeostasis. Suitable anti-microbial agents for use in the wetting composition of the present invention include, for example, anti-fungal agents, anti-bacterial agents, anti-viral agents, and antiseptic agents.

In one embodiment of the present invention, the anti-microbial agents are anti-fungal agents. Suitable anti-fungal agents for use in the wetting composition of the present invention include, for example, azoles or imidazoles, including but not limited to, miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole and their pharmaceutically acceptable salts and the like. Other suitable anti-fungal agents for use in the wetting composition of the present invention include, for example, an allylamine or an anti-fungal agent from another chemical family including, for example, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

In another embodiment of the present invention, the anti-microbial agents are anti-bacterial agents. Suitable anti-bacterial agents for use in the wetting composition of the present invention include, for example, chlorohexidine gluconate, sodium polystyrene sulfonate, sodium cellulose sulfate, silver particles of micro- and sub-micrometer sizes, silver salts and other anti-bacterial agents known to the art.

In still another embodiment of the present invention, the anti-microbial agents are anti-viral agents. Suitable anti-viral agents for use in the wetting composition of the present invention include, for example, immunomodulators, more preferably imiquimod, imiquimod derivatives, podofilox, podophyllin, interferon alpha, reticolos, cidofovir, nonoxynol-9, their pharmaceutically acceptable salts, and the like.

In yet another embodiment of the present invention, the anti-microbial agents are antiseptic agents. Suitable antiseptic agents for use in the wetting composition of the present invention include, for example, quaternary ammonium compounds, mercury compounds, and iodine compounds. Additional suitable antiseptic agents for use in the wetting composition of the present invention include, for example, benzalkonium chloride, benzethonium chloride, cetrimide, chlorhexidine, hexachlorophene, alcohol, hydrogen peroxide, hexamine hippurate, iodine, triclosan, cetylpyridinium chloride, and dequalinium chloride.

In an alternative embodiment of the present invention, the wetting composition may additionally include a broad spectrum anti-microbial agent. As used herein, the term "broad spectrum anti-microbial agent" is meant to include anti-microbial agents that are substantially equally effective in inhibiting the growth of, or killing, Gram negative bacteria, Gram positive bacteria, and yeast. By introducing a broad spectrum anti-microbial agent into the wet wipe product, alone or in addition to another anti-microbial agent, the anti-microbial agents will substantially inhibit the growth of, or kill, the problematic bacteria and yeast, while only having a slightly negative impact on the beneficial flora due to the broad spectrum anti-microbial agent. After application to the skin or mucosa of the wet wipe, the skin is left cleaned and with beneficial flora on the surface thereof.

The broad spectrum anti-microbial agent can be any broad spectrum anti-microbial agent suitable for use on the skin which is substantially non-antagonistic to the other components of the wet wipe product. The broad spectrum anti-microbial agent can be a synthetic anti-microbial agent, or it can be a naturally occurring anti-microbial agent. In a preferred embodiment, the broad spectrum anti-microbial agent is a natural broad spectrum anti-microbial agent, such as a botanical extract, herb or essential oil.

Suitable synthetic-type broad spectrum anti-microbial agents include, for example, alcohols having from one to about 6 or 7 carbon atoms per molecule. Alcohols exhibit anti-microbial properties when used at sufficiently high concentrations and/or with viscosity increasing agents (e.g., thickeners) to increase the residence time of the alcohol on the skin or mucosa. Other suitable synthetic-type broad spectrum anti-microbial agents include triclosan (2,4,4'-trichloro-2'-hydroxydiphenyl ether), triclocarban, p-chloro-m-xylenol, benzalkonium chloride, chlorohexidine gluconate, hexachlorophene and the like, and combinations thereof.

Suitable natural broad spectrum anti-microbial agents include, for example, aloe vera, folic acid, calendula flower, echinacea purpurea tops, gota kola extract, chlorophyll, phytoplenolin extract, chamomile flower, blood root, prickly ash bark, green tea leaf, oregano leaf, lavender oil, bio-saponin concentrate, olive leaf extract, black walnut green hulls, clove leaf, thyme herb, grapefruit seed extract, vegetable glycerin, and combinations thereof.

Where the wet wipe product of the present invention additionally comprises an anti-microbial agent, the wet wipe product may be used for treating or preventing bacterial vaginosis and/or vulvovaginal candidasis comprising wiping the skin or mucosa with the wet wipe product. The wet wipe product may also be used for treating or preventing Tinea cruris (jock-itch) and the like comprising wiping the skin or mucosa with the wet wipe product.

Pharmaceutical or Treatment Agents

The wetting composition may also contain one or more pharmaceutical or treatment agents. Suitable pharmaceutical or treatment agents for use in the wetting composition of the present invention include, for example, hormones, antibiotics, anesthetics, analgesics, immunodilators, contraceptives, and the like.

In one embodiment of the present invention, the wetting composition of the present invention additionally includes compositions comprising hormones for treating a decrease in estrogen secretion in the woman in need of estrogen replacement. Suitable hormones for use in the wetting composition of the present invention include, for example, estrogen selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, quinestrol and mestranol.

In another embodiment of the present invention, the wetting agent comprising one or more polyols may be useful for treating female sexual dysfunction without the use of other pharmaceutical or treatment agents, as the polyols may serve to increase blood flow to areas upon which the wet wipe is applied by increasing the temperature thereon. Alternatively, the wetting agent may further comprise pharmaceutical or treatment agents known to those of skill in the art to treat female sexual dysfunction, including such female sexual dysfunction disorders as female sexual arousal disorder, hypoactive sexual desire disorder, orgasmic disorder, and the like. The wetting agent of the present invention may also contain pharmaceutical or treatment agents known to those of skill in the art to treat dyspareunia and/or vaginismus, or vulvodynia and to relieve painful intercourse. Suitable pharmaceutical or treatment agents for these purposes include, for example, hormones such as estrogen, prostaglandin, testosterone, calcium channel blockers, cholinergic modulators, alpha-adrenergic receptor antagonist, beta-adrenergic receptor agonists, camp-dependent protein kinase activators, superoxide scavengers, potassium channel activators, estrogen-like compounds, testosterone-like compounds, benzodiazepines, adrenergic nerve inhibitors, HMG-COA reductase inhibitors, smooth muscle relaxants, adenosine receptor modulators and adenylyl cyclase activators, such as phosphodiesterase-5 inhibitors, and the like.

In one embodiment of the present invention, the wetting composition additionally includes one or more antibiotics. Suitable antibiotics for use in the wetting composition of the present invention include, for example, metronidazole, clindamycin, tinidazole, ornidazole, secnidazole, refaximin, trospectomycin, purpuromycin, their pharmaceutically acceptable salts, and the like.

In another embodiment of the present invention, the wetting composition additionally includes one or more anesthetics. Suitable anesthetics for use in the wetting composition of the present invention include, for example, benzocaine, lidocaine, dibucaine, benzyl alcohol, camphor, resorcinol, menthol, diphenhydramine hydrochloride, and the like.

In still another embodiment of the present invention, the wetting composition additionally includes one or more analgesics and/or nonsteroidal anti-inflammatory agents for treating ailments such as dysmenorrhea or menstrual cramping. Suitable analgesics for use in the wetting composition of the present invention include, for example, aspirin, ibuprofen, indomethacin, phenylbutazone, bromfenac, fenamate, sulindac, nabumetone, ketorolac, naproxen, and the like. Additionally, the wetting composition comprising one or more polyols may also be used for treating dysmenorrhea or menstrual cramping without additional additives in the wetting composition, as the polyols may serve to increase blood flow to areas upon which the wet wipe is applied by increasing the temperature thereon.

In a further embodiment of the present invention, the wetting composition additionally includes one or more contraceptives. Suitable contraceptives for use in the wetting composition of the present invention include, for example, nonoxynol-9, octoxynol-9, dodecaethyleneglycol monolaurate, Laureth 10s, Methoxypolyoxyethyleneglycol 550 Laurate, and the like.

Additional Additives

In order to still further enhance the benefits to consumers, a variety of additional additives can be incorporated into the wetting composition without jeopardizing the strength and dispersibilty functions of the wet wipe of the present invention. Suitable additional additives for use in the wetting composition of the present invention include, for example, odor control additives, microcapsules and other delivery vehicles, preservatives and anti-microbial agents, wetting agents and cleaning agents, surface feel modifiers, fragrances, fragrance solubilizers, opacifiers, pH control agents, and the like. The wet wipe of the present invention acts as a vehicle to deliver these additional additives to the skin or mucosa when applied thereon. Where the wetting composition comprises one or more polyols, the polyols therein may be used to enhance the absorption of additives in the wetting composition through the skin or mucosal tissue when applied thereon.

Odor Control Additives

Suitable odor control additives for use in the wetting composition and wet wipes of the present invention may include, but are not limited to: zinc salts; talc powder; encapsulated perfumes (including microcapsules, macrocapsules, and perfume encapsulated in liposomes, vesicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; anti-microbial agents, including silver-loaded zeolites (e.g., AgION™ antimicrobial compound sold by AgION Technologies, located in Wakefield, Mass.); triclosan; kieselguhr; and, mixtures thereof. In addition to controlling odor from the body or body wastes, odor control strategies may also be employed to mask or control any odor of the treated fibrous substrate. The wetting composition may contain less than about 5 weight percent of odor control additives based on the total weight of the wetting composition. More specifically, the wetting composition may contain from about 0.01 weight percent to about 2 weight percent of odor control additives. Even more specifically, the wetting composition may contain from about 0.03 weight percent to about 1 weight percent of odor control additives.

In one embodiment of the present invention, the wetting composition and/or wet wipes may comprise derivatized cyclodextrins, such as hydroxypropyl beta-cyclodextrin in solution, which remain on the skin after wiping and provide an odor-absorbing layer. In other embodiments of the present invention, the odor source may be removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the wet wipe product.

Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104-112, Feb. 1999.

Microparticulates

The wetting composition of the present invention may be further modified by the addition of solid particulates or microparticulates. Suitable particulates may include, but are not limited to: mica, silica, alumina, calcium carbonate, kaolin, talc, and zeolites. The particulates may be treated with stearic acid or other additives to enhance the attraction or bridging of the particulates to the triggerable binder formulation, if desired. Also, two-component microparticulate systems, commonly used as retention aids in the papermaking industry, may also be used. Such two-component microparticulate systems generally comprise a colloidal particle phase, such as silica particles, and a water-soluble cationic polymer for bridging the particles to the fibers of the fibrous substrate to be formed. The presence of particulates in the wetting composition may serve one or more useful functions, such as: (1) increasing the opacity of the wet wipes; (2) modifying the rheology or reducing the tackiness of the wet wipe; (3) improving the tactile properties of the wet wipe; or, (4) delivering desired agents to the skin or mucosa via a particulate carrier, such as a porous carrier or a microcapsule. The wetting composition may contain less than about 25 weight percent of particulate based on the total weight of the wetting composition. More specifically, the wetting composition may contain from about 0.05 weight percent to about 10 weight percent of microparticulate. Even more specifically, the wetting composition may contain from about 0.1 weight percent to about 5 weight percent of microparticulate.

Microcapsules and Other Delivery Vehicles

Microcapsules and other delivery vehicles may also be used in the wetting composition of the present invention to provide skin-care agents; medications; comfort promoting agents, such as eucalyptus; perfumes; skin care agents; odor control additives; vitamins; powders; and, other additives to the skin or mucosa of the user. Specifically, the wetting composition may contain up to about 25 weight percent of microcapsules or other delivery vehicles based on the total weight of the wetting composition. More specifically, the wetting composition may contain from about 0.05 weight percent to about 10 weight percent of microcapsules or other delivery vehicles. Even more specifically, the wetting composition may contain from about 0.2 weight percent to about 5.0 weight percent of microcapsules or other delivery vehicles.

Microcapsules and other delivery vehicles are well known in the art. For example, POLY-PORE® E200, commercially available from Chemdal Corporation located in Arlington Heights, Ill., may be a delivery agent comprising soft, hollow spheres that can contain an additive at over 10 times the weight of the delivery vehicle. Additives that may be used with POLY-PORE® E200 include, but are not limited to: benzyl peroxide, salicylic acid, retinol, retinyl palmitate, octyl methoxycinnamate, tocopherol, silicone compounds (DC 435), and mineral oil. Another delivery vehicle that may be used in the present invention is a sponge-like material commercially available under the trade designation of POLY-PORE® L200 from Chemdal Corporation, with silicone (DC 435) and mineral oil. Other delivery systems may include cyclodextrins and their derivatives, liposomes, polymeric sponges, and spray-dried starch.

Additives present in microcapsules may be isolated from the environment and the other agents in the wetting composition until the wet wipe is applied to the skin or mucosa, whereupon the microcapsules break and deliver their load to the skin or other surfaces.

Preservatives and Anti-Microbial Agents

The wetting composition of the present invention may also contain preservatives and/or anti-microbial agents for cleaning and/or sanitizing uses. Several preservatives and/or anti-microbial agents, such as Mackstat H 66 (commercially available from McIntyre Group located in Chicago, Ill.), may prevent bacteria and mold growth. Other preservatives and anti-microbial agents may include, but are not limited to: DMDM hydantoin, e.g., commercially available under the trade designation of Glydant Plus™ from Lonza, Inc. located in Fair Lawn, N.J.; iodopropynyl butylcarbamate; Kathon commercially available from Rohm and Hass located in Philadelphia, Pa.; methylparaben; propylparaben; 2-bromo-2-nitropropane-1,3-diol; benzoic acid; benzalkonium chloride; benzethonium chloride; and, the like. The wetting composition may contain less than about 2 weight percent on an active basis of preservatives and/or anti-microbial agents based on the total weight of the wetting composition. More specifically, the wetting composition may contain from about 0.01 weight percent to about 1 weight percent of preservatives and/or anti-microbial agents. Even more specifically, the wetting composition may contain from about 0.01 weight percent to about 0.5 weight percent of preservatives and/or anti-microbial agents. Further discussion regarding preservatives and/or anti-microbial agents may be found in Disinfection, Sterilization, and Preservation, 4th Edition, Lea & Frebiger, (1991), the disclosure of which is incorporated by reference to the extent it is non-contradictory herewith.

Wetting Agents and Cleaning Agents

A variety of wetting agents and/or cleaning agents may be used in the wetting composition of the present invention.

Suitable wetting agents and/or cleaning agents may include, but are not limited to; detergents and nonionic, amphoteric, cationic, and anionic surfactants. The wetting composition may contain less than about 3 weight percent of wetting agents and/or cleaning agents based on the total weight of the wetting composition. More specifically, the wetting composition may contain from about 0.01 weight percent to about 2 weight percent of wetting agents and/or cleaning agents. Even more specifically, the wetting composition may contain from about 0.1 weight percent to about 0.5 weight percent of wetting agents and/or cleaning agents. Suitable cationic surfactants may include, but are not limited to, quaternary ammonium alkyl halides like cetyl trimethyl ammonium chloride and cetyl trimethyl ammonium bromide.

Amino acid-based surfactant systems, such as those derived from amino acids L-glutamic acid and other natural fatty acids, may offer pH compatibility to human skin and good cleansing power, while being relatively safe and providing improved tactile and moisturization properties compared to other anionic surfactants. One function of the surfactant may be to improve wetting of the dry fibrous substrate with the wetting composition. Another function of the surfactant may be to disperse bathroom soils when the wet wipe contacts a soiled area and to enhance their absorption into the fibrous substrate. The surfactant may assist in make-up removal, general personal cleansing, hard surface cleansing, odor control, and the like. One commercially available example of an amino-acid based surfactant is acylglutamate, marketed under the trade designation of Amisoft from Ajinomoto Corporation located in Tokyo, Japan.

Suitable non-ionic surfactants may include, but are not limited to, the condensation products of ethylene oxide with a hydrophobic (oleophilic) polyoxyalkylene base formed by the condensation of propylene oxide with propylene glycol. The hydrophobic portion of these compounds may have a molecular weight sufficiently high so as to render it water-insoluble. The addition of polyoxyethylene moieties to this hydrophobic portion increases the water-solubility of the molecule as a whole, and the liquid character of the product may be retained up to the point where the polyoxyethylene content is about 50% of the total weight of the condensation product. Examples of compounds of this type include commercially available Pluronic surfactants from BASF Wyandotte Corporation located in Wyandotte, Mich., especially those in which the polyoxypropylene ether has a molecular weight of about 1500 to about 3000 and the polyoxyethylene content is about 35% to about 55% of the molecule by weight, i.e., Pluronic L-62.

Other useful nonionic surfactants may include, but are not limited to, the condensation products of $C_8$ to $C_{22}$ alkyl alcohols with 2 to 50 moles of ethylene oxide per mole of alcohol. Examples of compounds of this type may include the condensation products of $C_{11}$ to $C_{15}$ secondary alkyl alcohols with 3 to 50 moles of ethylene oxide per mole of alcohol, which are commercially available under the trade designation of the Poly-Tergent SLF series from Olin Chemicals located in Baltimore City, Md. or the TERGITOL® series from Union Carbide located in Danbury, Conn.; i.e., TERGITOL® 25-L-7, which is formed by condensing about 7 moles of ethylene oxide with a $C_{12}$ to $C_{15}$ alkanol.

Other nonionic surfactants, which may be employed in the wetting composition of the present invention, may include the ethylene oxide esters of $C_6$ to $C_{12}$ alkyl phenols such as (nonylphenoxy)polyoxyethylene ether. Esters prepared by condensing about 8 to 12 moles of ethylene oxide with nonylphenol, i.e., the IGEPAL® CO series commercially available from GAF Corporation located in Wayne, N.J. may be used in the wetting composition of the present invention.

Further non-ionic surface active agents may include, but are not limited to, alkyl polyglycosides (APG) derived as a condensation product of dextrose (D-glucose) and a straight or branched chain alcohol. The glycoside portion of the surfactant may provide a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is commercially available from Henkel Corporation located in Ambler, Pa. under the trade designations of Glucopon 220, Glucopon 225 and Glucopon 425.

Silicones are another class of wetting agents that may be available in pure form, or as microemulsions, macroemulsions, and the like. One non-ionic surfactant group is the silicone-glycol copolymers. These surfactants may be prepared by adding poly(lower)alkylenoxy chains to the free hydroxyl groups of dimethylpolysiloxanols and are commercially available from the Dow Corning Corporation located in Midland, Mich. under the trade designations of Dow Corning 190 and Dow Corning 193 surfactants (CTFA name: dimethicone copolyol). These surfactants may function, with or without any volatile silicones used as solvents, to control foaming produced by the other surfactants, and also may impart a shine to metallic, ceramic, and glass surfaces.

Anionic surfactants may also be used in the wetting compositions of the present invention. Anionic surfactants, which may be useful due to their high detergency, include anionic detergent salts having alkyl substituents of 8 to 22 carbon atoms such as the water-soluble higher fatty acid alkali metal soaps, e.g., sodium myristate and sodium palmitate. One class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples commercially available under the trade designation of the Bio-Soft series, i.e., Bio-Soft D-40 from Stepan Chemical Co. located in Northfield, Ill.

Other useful classes of anionic surfactants may include, but are not limited to: sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$ to $C_{16}$-alphaolefin sulfonates such as the Bio-Terge series commercially available from Stepan Chemical Co.; alkali metal salts of sulfated ethyleneoxy fatty alcohols (the sodium or ammonium sulfates of the condensation products of about 3 moles of ethylene oxide with a $C_{12}$ to $C_{15}$ n-alkanol, i.e., the Neodol ethoxysulfates commercially available from Shell Chemical Co. located in Houston, Tex.; alkali metal salts of higher fatty esters of low molecular weight alkylol sulfonic acids, e.g., fatty acid esters of the sodium salt of isothionic acid and the fatty ethanolamide sulfates; the fatty acid amides of amino alkyl sulfonic acids, e.g., lauric acid amide of taurine; as well as numerous other anionic organic surface active agents such as sodium xylene sulfonate, sodium naphthalene sulfonate, sodium toulene sulfonate; and, mixtures thereof.

A further useful class of anionic surfactants may includes the 8-(4-n-alkyl-2-cyclohexenyl)-octanoic acids, wherein the cyclohexenyl ring is substituted with an additional carboxylic acid group. These compounds or their potassium salts are commercially available from Westvaco Corporation located in Meriden, Conn. under the trade designations of Diacid 1550 or H-240. In general, these anionic surface active agents may be employed in the form of their alkali metal salts, ammonium or alkaline earth metal salts.

Surface Feel Modifiers

Surface feel modifiers may be used to improve the tactile sensation (e.g., lubricity) of the skin or mucosa during use of the cleaning or personal care product. Suitable surface feel modifiers include, but are not limited to, commercial debonders and softeners, such as the softeners used in the art of tissue making including quaternary ammonium compounds with fatty acid side groups, silicones, waxes, and the like. Quaternary ammonium compounds that may have utility as softeners are disclosed in U.S. Pat. No. 3,554,862, issued to Hervey et al. on Jan. 12, 1971; U.S. Pat. No. 4,144,122, issued to Emanuelsson et al. on Mar. 13, 1979; U.S. Pat. No. 5,573,637, issued to Ampulski et al. on Nov. 12, 1996; and, U.S. Pat. No. 4,476,323, issued to Hellsten et al. on Oct. 9, 1984, the disclosures of which are incorporated by reference to the extent that they are non-contradictory herewith. The wetting composition may contain less than about 2 weight percent of surface feel modifiers based on the total weight of the wetting composition. More specifically, the wetting composition may contain from about 0.01 weight percent to about 1 weight percent of surface feel modifiers. Even more specifically, the wetting composition may contain from about 0.01 weight percent to about 0.05 weight percent of surface feel modifiers.

In one embodiment of the present invention, where the insolubilizing agent is at least one polyol, the polyol itself functions as a surface feel modifier, lubricating agent, and/or moisturizing agent. Where the polyols additionally act as surface feel modifiers, lubricity is transferred from the wet wipe of the present invention to the skin or mucosa when applied thereon. The polyols increase in temperature when exposed to moisture from the skin or mucosa, thus acting as a warming, soothing, and lubricating agent.

Fragrances

A variety of fragrances may be used in the wetting composition of the present invention. The wetting composition may contain less than about 2 weight percent of fragrances based on the total weight of the wetting composition. More specifically, the wetting composition may contain from about 0.01 weight percent to about 1 weight percent of fragrances. Even more specifically, the wetting composition may contain from about 0.01 weight percent to about 0.05 weight percent of fragrances.

Fragrance Solubilizers

Further, a variety of fragrance solubilizers may be used in the wetting composition of the present invention. Suitable fragrance solubilizers may include, but are not limited to: polysorbate 20; propylene glycol; ethanol; isopropanol; diethylene glycol monoethyl ether; dipropylene glycol; diethyl phthalate; triethyl citrate; Ameroxol OE-2, commercially available from Amerchol Corporation located in Midland, Mich.; Brij 78 and Brij 98, commercially available from ICI Surfactants located in Wilmington, Del.; Arlasolve 200, commercially available from ICI Surfactants; Calfax 16L-35, commercially available from Pilot Chemical Co. located in Santa Fe Springs, Calif.; Capmul POE-S, commercially available from Abitec Corporation located in Columbus, Ohio; Finsolv SUBSTANTIAL, commercially available from Finetex located in Elmwood Park, N.J.; and, the like.

The wetting composition may contain less than about 2 weight percent of fragrance solubilizers based on the total weight of the wetting composition. More specifically, the wetting composition may contain from about 0.01 weight percent to about 1 weight percent of fragrance solubilizers. Even more specifically, the wetting composition may contain from about 0.01 weight percent to about 0.05 weight percent of fragrance solubilizers.

Opacifiers

Suitable opacifiers may include, but are not limited to, titanium dioxide or other minerals or pigments, and synthetic opacifiers, such as REACTOPAQUE® particles, commercially available from Sequa Chemicals, Inc. located in Chester, S.C. The wetting composition may contain less than about 2 weight percent of opacifiers based on the total weight of the wetting composition. More specifically, the wetting composition may contain from about 0.01 weight percent to about 1 weight percent of opacifiers. Even more specifically, the wetting composition may contain from about 0.01 weight percent to about 0.05 weight percent of opacifiers.

pH Control Agents pH control agents for use in the wetting composition of the present invention may include, but are not limited to; malic acid; citric acid; hydrochloric acid; acetic acid; sodium hydroxide; potassium hydroxide; and, the like. An appropriate pH range minimizes the amount of skin irritation resulting from the wetting composition on the skin. The pH range of the wetting composition may range from about 3.5 to about 6.5. More specifically, the pH range of the wetting composition may range from about 4 to about 6. The overall pH of the wet wipe product; i.e., the complete wet wipe product including the fibrous substrate portion and the wetting composition portion, may range from about 4.5 to about 5.5; more specifically, about 5.0. The wetting composition may contain less than about 2 weight percent of a pH adjuster based on the total weight of the wetting composition. More specifically, the wetting composition may contain from about 0.01 weight percent to about 1 weight percent of a pH adjuster. Even more specifically, the wetting composition may contain from about 0.01 weight percent to about 0.05 weight percent of a pH adjuster.

Other Additional Components

It should be noted that the above-described wetting compositions of the present invention may be used with any one of the above-described triggerable binder compositions of the present invention. Further, the above-described wetting compositions of the present invention may be used with any other binder composition, including conventional binder compositions, or with any known fibrous or absorbent substrate, whether dispersible or not.

Method of Making Wet Wipes

The wet wipes of the present invention may be made in several ways. In one embodiment of the present invention, the triggerable binder formulation may be applied to a fibrous substrate as part of an aqueous solution or suspension, wherein subsequent drying is needed to remove the water and promote binding of the fibers within the fibrous substrate. In particular, during drying, the triggerable binder formulation migrates to the crossover points of the fibers and becomes activated as a triggerable binder formulation in those regions, thus providing acceptable strength to the fibrous substrate. By way of example, the following steps are provided and may be applied:

1. Providing an absorbent fibrous substrate that is not highly bonded (e.g., an unbonded air-laid, a tissue web, a carded web, fluff pulp, etc.);

2. Applying a triggerable binder formulation to the fibrous substrate, typically in the form of a liquid, suspension, or foam;

3. Drying the fibrous substrate to promote bonding of the fibers within the fibrous substrate;

4. Applying a wetting composition to the fibrous substrate thereby providing a wetted product; and, 5. Placing the wetted product in roll form or in a stack and packaging the wetted product.

Alternatively, the dry product may be placed in roll form or in a stack and packaged after the completion of steps 1-3 above, followed thereafter by the addition of the wetting composition. The wetted product could then be either used immediately, or repackaged for future use.

Application of the triggerable binder formulation to the fibrous substrate may be accomplished by means of spray application; foam application; immersion in a bath; curtain coating; coating and metering with a wire-wound rod; passage of the fibrous substrate through a flooded nip; contact with a pre-metered wetted roll coated with the triggerable binder formulation; by pressing the fibrous substrate against a deformable carrier containing the triggerable binder formulation such as a sponge or felt to effect transfer into the fibrous substrate; printing such as gravure, inkjet, or flexographic printing; and, any other means known to one skilled in the art. In the alternative, wet-end application is acceptable.

Without wishing to be bound by theory, it is believed that a drying step after application of the triggerable binder formulation and before application of the wetting composition may enhance bonding of the fibers within a fibrous substrate by driving the triggerable binder formulation to fiber crossover points as moisture is driven off, thus promoting efficient use of the triggerable binder formulation. However, in an alternative method, the drying step discussed above may be skipped, and the triggerable binder formulation may be applied to the fibrous substrate followed by application of the wetting composition without significant intermediate drying. In one embodiment of this method, the triggerable binder formulation may selectively adhere to the fibers, permitting excess water to be removed in an optional pressing step without a significant loss of the triggerable binder formulation from the fibrous substrate. In another embodiment of this method, no significant water removal need occur prior to application of the wetting composition. In yet another alternative embodiment of this method, the triggerable binder formulation and the wetting composition may be applied simultaneously to the fibrous substrate, optionally with subsequent addition of additives or insolubilizing agents to further render the triggerable binder formulation insoluble.

The present invention may be further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Wetting Composition Preparation

ACS reagent grade or better of isopropanol (IPA), acetone (ACE), t-butyl alcohol (TBA), n-butyl alcohol (NBA), n-propanol (NPA), ethanol (EtOH) or methanol (MeOH) were used in formulating the wetting solutions used in the following examples. The concentrations of these insolubilizing agents in the wetting compositions ranged between 60% and 100% (neat). Where the concentration of the insolubilizing agents in the wetting compositions was below 100%, insolubilizing agent was combined with deionized water.

Fibrous Substrate Sample Preparation

Two different fibrous substrates were used to evaluate the performance of the triggerable binder formulation: UCTAD tissue and thermally-bonded air-laid nonwoven.

UCTAD Tissue

An uncreped through-air dried (UCTAD) tissue fibrous substrate with a basis weight of about 50 gsm and a caliper of about 1.3 mm was used to evaluate samples of the triggerable binder formulations. Eucalyptus wood pulp fibers are commercially available from Aracruz located in the Brazilian states of Espirito Santo, Rio Grande do Sul and Eunapolis. LL-19 wood pulp fibers are commercially available from Neenah Paper Corporation located in Neenah, Wisconsin. These fibers were used to form the fibrous substrates. The eucalyptus and LL-19 wood pulp fibers were dispersed into water to form an eucalyptus pulp fiber slurry and a LL-19 pulp fiber slurry. A 3-layer headbox was utilized to deposit the pulp fiber slurries in a 30/40/30 split of eucalyptus/LL-19/eucalyptus wood pulp fibers into a fibrous substrate. The substrate was rush-transferred to a transfer fabric (T807-1 from Voith Fabrics of Appleton, Wis.). The transfer fabric was traveling 28-30 percent slower than the forming fabric using a vacuum shoe to assist the transfer. At a second vacuum shoe-assisted transfer, the substrate was transferred and wet-molded onto the throughdrying fabric (T1203-8 from Voith Fabrics of Appleton, Wis.). The sheet was dried with a throughdryer operating at a temperature of approximately 290° F. Targeted ranges of geometric mean tensile (GMT) and tensile ratio were 1500-2000 and 1.2-1.5, respectively. The UCTAD fibrous substrate had no residual wet strength in water.

Thermally-Bonded Air-Laid Nonwoven

A weak, thermally-bonded air-laid (TBAL) nonwoven fibrous substrate was fabricated using Weyerhauser NF405 wood pulp fibers (Weyerhauser Company, Federal Way, Wash.) and KOSA polyester staple type-255 binder fibers (available from Invista™, with offices in Wichita, Kans.). The T-255 binder fibers had a polyester core and a polyethylene sheath that melts at about 130° C. The air-laid fibrous substrate was formed using about 4% T-255 binder fibers and thermally bonded above the melting temperature of the polyethylene sheath. The TBAL fibrous substrate samples have an average basis weight of about 51 gsm and an average caliper of about 1.0 mm. The TBAL fibrous substrate samples have a residual CD wet tensile strength of about 30 g/in. in water. Unless otherwise noted, the data for the TBAL fibrous substrate samples have been corrected for this residual wet strength. The application and drying methods used for the treatments of the triggerable binder formulation are those described above for the UCTAD fibrous substrate samples.

Topical Application Method for Triggerable Binder Formulation

A uniform and consistent amount of each sample of triggerable binder formulation was applied to the fibrous substrate via a pressurized handsheet spray unit. This handsheet spray unit is designed to closely resemble the operation of a commercial air-laid machine using liquid or emulsion binders, but on a smaller pilot scale. The handsheet spray unit is enclosed in a small-framed housing, which may be placed, under a laboratory hood. The handsheet spray unit has a stationary sample holder section (10"×13") in the center of the unit and a moveable spray header directly over the sample holder section. A vacuum box is installed under the sample holder section to help draw the triggerable binder formulation into the fibrous substrate during the application process. The fibrous substrate sample is placed on the vacuum box and the spray head is moved across the fibrous substrate sample as the triggerable binder formulation is sprayed in a flat V-shaped pattern. The triggerable binder formulation is contained in a pressurized storage vessel located outside of the spray cabinet and is delivered to the spray nozzles via high pressure flexible tubing. The spray header with its spray nozzle assembly (commercially available from Spraying Systems Company located in Wheaton, Ill.) is moved over the sample by means of a belt driven slide assembly, providing the desired application uniformity and speed. The spray header may be operated at speeds close to 180 fpm and the spray atomization pressure could be set as high as 200 psig. Approximately one half of the desired weight of the triggerable binder formulation is applied to the first side of each fibrous substrate sample. Each fibrous substrate sample is then manually turned over and the remaining desired weight of the triggerable binder formulation is applied to the second side. The fibrous substrate sample is manually removed and dried in a Wemer Mathis, Model LTV Through-Air Dryer (TAD) at 193° C. for about 20 seconds to about 40 seconds.

In-Use Tensile Strength and Disposal Strength Testing

A SinTech 1/D tensile tester with Testworks 3.03 version software is used for all sample testing. A 100 Newton load cell with pneumatic grips is utilized. A gauge length of 2 inch and a crosshead speed of 12 inch/minute are employed. The peak load values (in g/in.) of sample replicates are recorded and averaged and reported as machine-direction wet tensile strength (MDWT) or cross-deckle wet tensile strength (CDWT), depending on how the measurement was made.

The in-use strength of each fibrous substrate sample is simulated by soaking 1 inch by 4.5 inch strip fibrous substrate samples in an excess of wetting composition containing the desired insolubilizing agent. The fibrous substrate samples are allowed to equilibrate for at least 12 hours before measurements of the tensile strength of each fibrous substrate samples are taken. The disposal strength or dispersibility is assessed by transferring the fibrous substrate samples treated as "in-use" into an excess (typically 500 mL for 4 to 8 strips of fibrous substrate samples) of deionized water or hard water of specified hardness level (as metal ion) and allowing the fibrous substrate samples to soak for the indicated amount of time before the tensile strength of each fibrous substrate sample is measured. In cases where a soaked fibrous substrate sample is too weak to be handled or to allow measurements of the tensile strength to be taken, a value of zero is recorded for the peak load of the fibrous substrate sample.

Results

A non-crosslinking cationic polyacrylamide polymer, commercially available under the trade designation of Baystrength® 711 from Bayer Corporation located in Pittsburgh, Pa., was evaluated as a triggerable binder formulation on the UCTAD and TBAL fibrous substrate samples as described above. Unless otherwise stated, the Baystrength® 711 as used herein was a solution of 5% solids. The Baystrength® 711 polymer was applied to the fibrous substrate samples as described above. The triggerable binder formulation add-on level for each fibrous substrate sample was 5 wt. %. The treated fibrous substrate samples were allowed to equilibrate for in-use tensile strength measurements, as described above, in 100% and 65 wt. % isopropyl alcohol (IPA) wetting compositions. The tensile strength of the treated fibrous substrate samples is presented in Table 1.

TABLE 1

Performance of Baystrength ® 711 polymer at 5 wt. % triggerable binder formulation add-on level on TBAL and UCTAD fibrous substrates in IPA wetting compositions.

| Code | % IPA (overnight soak) | Basesheet | CDWT (g/in.) In-use | Std. Dev. | CDWT (g/in.) 10 min. Hard Water | Std. Dev. |
|---|---|---|---|---|---|---|
| 8635-47-1 | 100 | UCTAD | 944 | 35 | 0 | — |
| 8635-47-2 | 65 | UCTAD | 232 | 35 | 13 | 4 |
| 8635-47-3 | 100 | TBAL | 425 | 138 | 0 | — |
| 8635-47-4 | 65 | TBAL | 84 | 8 | 0 | — |

As used herein, the phrase "overnight soak" means a soak of about 16 to about 24 hours.

As shown in Table 1, the in-use tensile strength of the fibrous substrate samples depends on fibrous substrate type and the composition of the wetting composition. The UCTAD fibrous substrate sample showed significant in-use tensile strength in the 100% IPA wetting composition, possibly due to its inherent hydrogen bonding (about 325 g/in.). However, the in-use tensile strength of the UCTAD fibrous substrate sample is lower in the 65% IPA wetting composition, possibly due to the high water content. Higher in-use strength may be achieved in both fibrous substrate types by choosing a wetting composition having a higher alcohol content. Dispersibility or disposal strength, as indicate by 10 minute soaks in 200 ppm hard water (as metal ion), is very good for both fibrous substrate types.

Two wetting compositions having antiseptic and disinfecting properties were formulated. The Baystrength® 711 polymer was applied to the fibrous substrate samples as described above. The triggerable binder formulation add-on level for each fibrous substrate sample was 5 wt. %. The treated fibrous substrate samples were allowed to equilibrate for in-use tensile strength measurements in the formulated wetting compositions A and B. The in-use tensile strength of the treated fibrous substrate samples are presented in Table 2.

TABLE 2

Performance of Baystrength ® 711 polymer at 5 wt. % triggerable binder formulation add-on level on TBAL and UCTAD fibrous substrates in formulated wetting compositions A and B.

| Code | Solution (overnight soak) | Basesheet | CDWT (g/in.) In-use | Std. Dev. | CDWT (g/in.) 10 min. Hard Water | Std. Dev. |
|---|---|---|---|---|---|---|
| 8635-50-1 | A | UCTAD | 375 | 28 | 19 | 7 |
| 8635-50-2 | A | TBAL | 175 | 52 | 2 | 5 |
| 8635-50-3 | B | UCTAD | 704 | 49 | 9 | 11 |
| 8635-50-4 | B | TBAL | 463 | 40 | 1 | 5 |

Solution A: 65% IPA, 8% Propylene glycol, 27% Water

Solution B: 75% IPA, 12% Propylene glycol, 13% Water

As shown in Table 2, the in-use tensile strength of the treated fibrous substrate samples depends on the fibrous substrate type and the composition, namely the water content, in the wetting composition. The dispersibility or disposal strength for both fibrous substrate types is good.

EXAMPLE 2

An anionic polyacrylamide polymer, commercially available under the trade designation of Baystrength® 85 from Bayer Corporation, was evaluated as a triggerable binder formulation on the UCTAD and TBAL fibrous substrate samples as described above. The Baystrength® 85 polymer was applied to the fibrous substrate samples as described above. The triggerable binder formulation add-on level for each fibrous substrate sample ranged from 1.8 wt. % to 10 wt. %. The treated fibrous substrate samples were allowed to equilibrate for in-use tensile strength measurements, as described above, in wetting compositions having an IPA content that ranged from 65% to 100%. Dry treated fibrous substrate samples were also tested for in-use tensile strength. The in-use tensile strength of the treated fibrous substrate samples, wet and dry, is presented in Table 3. The dispersibility or disposal strength of the treated fibrous substrate samples for 10 minute and 30 minute soaks in 200 ppm hard water are also presented in Table 3.

available from Kimberly-Clark Corporation, was used for evaluation of the Baystrength® 85 polymer as a triggerable binder formulation. This UCTAD fibrous substrate sample possesses a residual wet strength of about 40 g/in. in water. The results presented in Table 4 were not corrected for residual wet strength of the UCTAD fibrous substrate samples in this example. The Baystrength® 85 polymer was applied to the fibrous substrate samples as described above. The triggerable binder formulation add-on level for each fibrous substrate sample ranged from 2 wt. % to 5 wt. %. The in-use tensile strength and disposal strength for the treated fibrous substrate samples were evaluated as described in Example 1, with the exception that 100 ppm hard water (as metal ion) was utilized for soak tests. The treated fibrous substrate samples were allowed to equilibrate for in-use tensile strength measurements, as described above, in wetting compositions having an IPA content ranging from 65% to 100%, an ethanol (EtOH) content ranging from 80% to 100%, or a methanol (MeOH) content of 100%. The treated fibrous substrate samples were soaked in the hard water for disposal strength measurements for 10 minutes and 30 minutes. The in-use

TABLE 3

Performance of Baystrength ® 85 polymer at various triggerable binder formulation add-on levels on TBAL and UCTAD fibrous substrates in IPA wetting compositions.

| Code | % Binder | % IPA overnight soak | Basesheet | CDWT (g/in.) In-use | Std. Dev. | CDWT (g/in.) 10 min. Hard Water | Std. Dev. | CDWT (g/in.) 30 min. Hard Water | Std. Dev. |
|---|---|---|---|---|---|---|---|---|---|
| 1 | 1.8 | Dry | UCTAD | 1165 | 72 | — | — | — | — |
| 2 | 1.8 | 100 | UCTAD | 931 | 45 | 0 | — | 0 | — |
| 3 | 1.8 | 90 | UCTAD | 572 | 136 | 0 | — | 0 | — |
| 4 | 1.8 | 80 | UCTAD | 347 | 98 | 0 | — | 0 | — |
| 5 | 1.8 | 65 | UCTAD | 155 | 43 | 0 | — | 0 | — |
| 6 | 5.0 | Dry | UCTAD | 1741 | 71 | — | — | — | — |
| 7 | 5.0 | 100 | UCTAD | 1109 | 204 | 0 | — | 0 | — |
| 8 | 5.0 | 90 | UCTAD | 1090 | 223 | 0 | — | 0 | — |
| 9 | 5.0 | 80 | UCTAD | 617 | 212 | 0 | — | 0 | — |
| 10 | 5.0 | 65 | UCTAD | 223 | 83 | 0 | — | 0 | — |
| 11 | 6.9 | Dry | UCTAD | 1546 | 139 | — | — | — | — |
| 12 | 6.9 | 90 | UCTAD | 842 | 288 | 0 | — | 0 | — |
| 13 | 6.9 | 80 | UCTAD | 783 | 222 | 0 | — | 0 | — |
| 14 | 6.9 | 65 | UCTAD | 324 | 56 | 0 | — | 0 | — |
| 15 | 6.9 | 50 | UCTAD | 117 | 21 | 0 | — | 0 | — |
| 16 | 7.6 | Dry | TBAL | 547 | 83 | — | — | — | — |
| 17 | 7.6 | 90 | TBAL | 291 | 67 | 4 | 14 | 0 | 0 |
| 18 | 7.6 | 80 | TBAL | 204 | 94 | 14 | 29 | 29 | 0 |
| 19 | 7.6 | 65 | TBAL | 34 | 27 | — | — | — | — |
| 20 | 10 | Dry | TBAL | 936 | 266 | — | — | — | — |
| 21 | 10 | 100 | TBAL | 582 | 228 | 28 | 14 | 20 | 6 |
| 22 | 10 | 90 | TBAL | 633 | 43 | 8 | 4 | 6 | 36 |
| 23 | 10 | 80 | TBAL | 316 | 117 | 14 | 9 | 10 | 4 |
| 24 | 10 | 65 | TBAL | 51 | 17 | 22 | 9 | 13 | 5 |

As shown in Table 3, a broad range of in-use tensile strength and disposal strength may be achieved by the choice of the fibrous substrate type and the composition of the wetting composition.

EXAMPLE 3

An UCTAD fibrous substrate sample having a basis weight of about 45 gsm and a caliper of about 1.3 mm commercially tensile strength and disposal strength measurements of the treated fibrous substrate samples are presented in Table 4.

TABLE 4

Performance of Baystrength ® 85 polymer at various triggerable binder formulation add-on levels on UCTAD fibrous substrate in various wetting compositions.

| Binder % | Solvent > | CDWT (g/in.) | | | | | | |
|---|---|---|---|---|---|---|---|---|
| | | 65% IPA | 80% IPA | 90% IPA | 100% IPA | 80% EtOH | 100% EtOH | 100% MeOH |
| 2% | In-use | 174 | 388 | 739 | 936 | 463 | 543 | 475 |
| | std. dev. | 18 | 20 | 38 | 122 | 53 | 102 | 40 |
| | 10 min. soak | 39 | 38 | 39 | 41 | 42 | 40 | 38 |
| | std. dev. | 1 | 2 | 3 | 1 | 3 | 3 | 3 |
| | 30 min. soak | 41 | 41 | 36 | 44 | 43 | 41 | 40 |
| | std. dev. | 3 | 3 | 2 | 3 | 4 | 3 | 3 |
| 3% | In-use | 300 | 921 | 1009 | 1266 | 722 | 1082 | 1000 |
| | std. dev. | 10 | 22 | 77 | 64 | 102 | 3 | 50 |
| | 10 min. soak | 39 | 43 | 47 | 41 | 45 | 41 | 45 |
| | std. dev. | 7 | 7 | 4 | 4 | 1 | 2 | 1 |
| | 30 min. soak | 44 | 42 | 45 | 40 | 45 | 41 | 43 |
| | std. dev. | 1 | 1 | 3 | 2 | 5 | 3 | 2 |
| 4% | In-use | 373 | 862 | 1399 | 1294 | 845 | 1438 | 1283 |
| | std. dev. | 5 | 56 | 79 | 192 | 100 | 94 | 70 |
| | 10 min. soak | 42 | 42 | 44 | 47 | 45 | 43 | 39 |
| | std. dev. | 3 | 4 | 3 | 3 | 5 | 1 | 5 |
| | 30 min. soak | 44 | 44 | 43 | 45 | 44 | 45 | 46 |
| | std. dev. | 2 | 3 | 1 | 3 | 2 | 1 | 7 |
| 5% | In-use | 442 | 1073 | 1569 | 1296 | 965 | 1561 | 1341 |
| | std. dev. | 12 | 31 | 78 | 166 | 13 | 62 | 37 |
| | 10 min. soak | 39 | 45 | 40 | 40 | 44 | 39 | 42 |
| | std. dev. | 4 | 0 | 6 | 6 | 3 | 4 | 5 |
| | 30 min. soak | 37 | 45 | 35 | 46 | 42 | 41 | 40 |
| | std. dev. | 3 | 5 | 7 | 4 | 1 | 3 | 5 |

As shown in Table 4, the triggerable binder formulation add-on levels, insolubilizing agent, and the composition of the wetting composition may be chosen to provide a targeted in-use tensile strength or disposal strength. The disposal strength of the treated fibrous substrate samples returns to the level of the residual wet strength of the fibrous substrate sample during soaks in the hard water within 10 minutes or less.

EXAMPLE 4

The TBAL fibrous substrate sample from Example 1 was used to evaluate the Baystrength® 85 polymer as a triggerable binder formulation. The Baystrength® 85 polymer was applied to the fibrous substrate samples as described above. The triggerable binder formulation add-on level for each fibrous substrate was 5 wt. %. The in-use tensile strength and disposal strength for the treated fibrous substrate samples were evaluated as described in Example 1. The treated fibrous substrate samples were allowed to equilibrate for in-use tensile strength measurements, as described above, in wetting compositions of neat insolubilizing agents as provided in Table 5 below. The use of neat insolubilizing agents allowed for the examination of the relationship of the Solubility Parameter theory to the in-use tensile strength of the fibrous substrate samples. Methanol (MeOH), ethanol (EtOH), n-propanol (NPA), isopropanol (IPA), n-butanol (NBA), tert-butanol (TBA), acetone (ACE), and propylene glycol (PPG) were utilized as insolubilizing agents. The Baystrength® 85 polymer has a δ value of about 21 $(cal/cm^3)^{1/2}$. According to Solubility Parameter theory, solvents having similar δ values to that of an acceptable solvent would be acceptable as solvents as well. In addition, solvents having dissimilar δ values to an acceptable solvent would not be an acceptable solvent. Water, having a δ of 23.4 $(cal/cm^3)^{1/2}$, is known to be an excellent solvent for polyacrylamide polymer, leading to good dispersibility of fibrous substrates of the present invention treated with such a triggerable binder formulation. In accordance with the theory, one might predict that solvent having a δ value with the largest difference from the δ value of water would yield the highest in-use tensile strength. In general, such a trend is seen, within experimental error, for the groups of solvents investigated as insolubilizing agents, with the exception of the tertiary alcohol, TBA. Note that CDWT of the TBAL fibrous substrate samples not treated with the triggerable binder formulation in selected solubilizing agents show only in-use tensile strength values that reflect residual strength levels of the fibrous substrate samples.

TABLE 5

In-use tensile strength of TBAL fibrous substrates is various insolubilizing agents for the Baystrength ® 85 polymer as a triggerable binder formulation.

| Solvent | $\delta(cal/cm3)^{0.5}$ | CDWT (g/in.) | Std.Dev. |
|---|---|---|---|
| MeOH | 14.5 | 455 | 21 |
| EtOH | 12.7 | 618 | 34 |
| PPG | 12.6 | 762 | 47 |
| NPA | 11.9 | 737 | 74 |
| IPA | 11.5 | 768 | 51 |
| NBA | 11.4 | 851 | 24 |
| TBA | 10.6 | 646 | 25 |
| ACE | 9.9 | 838 | 75 |
| Dry TBAL | 5% Binder | 758 | 25 |
| MeOH | TBAL no binder | 22 | 2 |
| IPA | TBAL no binder | 37 | 3 |
| ACE | TBAL no binder | 32 | 2 |
| Dry TBAL | no binder | 36 | 8 |

EXAMPLE 5

An anionic polyacrylamide polymer, commercially available under the trade designation of Hercobond® 2000 polymer from Hercules Incorporated located in Wilmington, Del., was evaluated as a triggerable binder formulation. The Hercobond® 2000 polymer had a weight-average molecular weight ($M_w$) of about 400,000 g/mole. The performance of the Hercobond® 2000 polymer as a triggerable binder formulation was compared with Baystrength® 85 polymer on 6041 towel fibrous substrate samples commercially available from the Kimberly-Clark Corporation. The 6041 towel fibrous substrate samples have a basis weight of about 30 gsm and a caliper of about 0.5 mm. The 6041 towel fibrous substrate samples have a residual wet strength of about 60 gsm in water. The results presented in Table 6 were not corrected for residual wet strength of the 6041 towel fibrous substrate samples of this example. The Hercobond® 2000 polymer and the Baystrength® 85 polymer were applied to the 6041 towel fibrous substrate samples as described above. The triggerable binder formulation add-on levels for each 6041 towel fibrous substrate sample of the Hercobond® 2000 polymer range from 2.1 wt. % to 4.1 wt. % and of the Baystrength® 85 polymer range from 1.9 wt. % to 4.0 wt. %. The in-use tensile strength and disposal strength for the treated 6041 towel fibrous substrate samples were evaluated as described in Example 1, with one exception. Due to the sheet size of the 6041 towel fibrous substrate samples and the configuration of the handsheet spray unit, the treated 6041 towel fibrous substrate samples were evaluated in machine direction of the fibrous substrate. The treated 6041 towel fibrous substrate samples were allowed to equilibrate for in-use tensile strength measurements, as described above, in a wetting composition having an IPA content of 80%. The treated 6041 towel fibrous substrate samples were soaked in the hard water for disposal strength measurements for 10 minutes and 30 minutes. The in-use tensile strength and disposal strength measurements of the treated 6041 towel fibrous substrate samples are presented in Table 6.

EXAMPLE 6

The performance of the Hercobond® 2000 polymer was compared with three other polyacrylamide polymers commercially available under the trade designations of SPP-949, SPP-376, and SPP-377 from Scientific Polymer Products, Incorporated located in Ontario, N.Y., as triggerable binder formulations on the UCTAD fibrous substrate samples as described in Example 1. The SPP-949 polymer is a nonionic polyacrylamide with molecular weight of about 10,000 g/mole. The SPP-376 polymer is a carboxyl modified polyacrylamide (having a low carboxyl content) with a molecular weight of about 200,000 g/mole. The SPP-377 polymer is a carboxyl modified polyacrylamide (having a high carboxyl content) with a molecular weight of about 200,000 g/mole. The Hercobond® 2000 polymer, SPP-949 polymer, SPP-376 polymer, and SPP-377 polymer were applied to the fibrous substrate samples as described above. The triggerable binder formulation add-on levels for each fibrous substrate sample of the Hercobond® 2000 polymer, SPP-949 polymer, SPP-376 polymer, and SPP-377 polymer were at 2.0 wt. %, 8.2 wt. %, 4.2 wt. %, and 4.4 wt. %, respectively. The in-use tensile strength and disposal strength for the fibrous substrate samples were evaluated as described in Example 1. The treated fibrous substrate samples were allowed to equilibrate for in-use tensile strength measurements, as described above, in wetting composition having an IPA content ranging from 80% to 100%. The treated fibrous substrate samples were soaked in the hard water for disposal strength measurements for 10 minutes. The in-use tensile strength and disposal strength measurements of the treated fibrous substrate samples are presented in Table 7.

TABLE 6

Performance of Hercobond ® 2000 polymer and Baystrength ® 85 polymer on 6041 towel fibrous substrates in 80% IPA wetting composition.

| Code | Binder | % Add-on | In-use (80% IPA) MDWT | std. dev | MDWT 10 min. soak | std. dev | MDWT 30 min. soak | std. dev |
|---|---|---|---|---|---|---|---|---|
| KCP 6041 | none | — | 329 | 13 | 60 | 13 | 62 | 15 |
| 8635-154A | Baystrength 85 | 4.0 | 1450 | 80 | — | — | — | — |
| 8635-154B | Baystrength 85 | 2.8 | 1213 | 47 | — | — | — | — |
| 8635-154C | Baystrength 85 | 1.9 | 1048 | 93 | 110 | 8 | 103 | 6 |
| 8635-155A | Hercobond 2000 | 4.1 | 1153 | 68 | — | — | — | — |
| 8635-155B | Hercobond 2000 | 3.1 | 1129 | 89 | — | — | — | — |
| 8635-155C | Hercobond 2000 | 2.1 | 1056 | 86 | 125 | 12 | 113 | 15 |

As presented in Table 6, both the Hercobond® 2000 polymer and the Baystrength® 85 polymer show high in-use tensile strength (greater than about 1000 g/in.) of the 6041 towel fibrous substrate samples treated with a triggerable binder formulation add-on level as low as 2 wt. %. However the disposal strength of the treated 6041 towel fibrous substrate samples appears to higher—thus the dispersibility of the treated 6041 towel fibrous substrate samples appear to be lower and/or slower. The 6041 towel fibrous substrate samples treated with about 2 wt. % add-on level of one of the triggerable binder formulations retained about 100 g/in. Disposal strength measurements were taken of the treated 6041 towel fibrous substrate samples after soaking for 30 minutes in hard water.

As shown in Table 7, the SPP-949 polymer requires slightly higher triggerable binder formulation add-on level to achieve a higher in-use tensile strength. The in-use tensile strength of the fibrous substrate samples treated with the SPP-949 polymer drops significantly when water is utilized in the wetting composition. The SPP-376 polymer and the SPP-377 polymer show good in-use tensile strength of the fibrous substrate samples in the wetting compositions having IPA contents of 100% and 80%. The in-use tensile strength of the fibrous substrate sample treated with the SPP-377 polymer drops significantly when water is utilized in the wetting composition. The fibrous substrate samples treated with the Hercobond® 2000 polymer, SPP-949 polymer, SPP-376 polymer, and SPP-377 polymer show good disposal strength.

TABLE 7

Comparison of Hercobond ® 2000 polymer with SPP-949 polymer, SPP-376 polymer, and SPP-377 polymer on UCTAD fibrous substrates in 80% and 100% IPA wetting compositions.

| Code | Binder | % Add-on | % IPA | In-use MDWT | std. dev. | MDWT 10 min. soak | std. dev. |
|---|---|---|---|---|---|---|---|
| 8635-184A | Hercobond 2000 | 2.0 | 100 | 974 | 40 | 31 | 14 |
| 8635-184A | Hercobond 2000 | 2.0 | 80 | 497 | 21 | 33 | 2 |
| 8635-185A | SPP-949 | 8.2 | 100 | 598 | 25 | 31 | 14 |
| 8635-185A | SPP-949 | 8.2 | 80 | 113 | 9 | — | — |
| 8635-186A | SPP-376 | 4.2 | 100 | 1079 | 132 | 18 | 7 |
| 8635-186A | SPP-376 | 4.2 | 80 | 783 | 51 | 16 | 8 |
| 8635-187A | SPP-377 | 4.4 | 100 | 1131 | 70 | 32 | 3 |
| 8635-187A | SPP-377 | 4.4 | 80 | 406 | 11 | 12 | 1 |

As shown in Table 7, the molecular weight and triggerable binder formulation may be chosen to provide a targeted in-use tensile strength or disposal strength.

EXAMPLE 7

Polyvinylamine/vinylformamide co-polymers, commercially available under the trade designation of Catiofast® 8104 co-polymer, Catiofast® 8087 co-polymer, and Catiofast® 8106 co-polymer from BASF located in Holly Springs, N.C., were evaluated as triggerable binder formulations on the TBAL fibrous substrate samples as described in Example 1. The Catiofast® 8104 co-polymer is a 10% hydrolyzed poly-N-vinylformamide. The Catiofast® 8087 co-polymer is a 50% hydrolyzed poly-N-vinylformamide. The Catiofast® 8106 co-polymer s a 90% hydrolyzed poly-N-vinylformamide. The Catiofast® 8104 co-polymer, Catiofast® 8087 co-polymer, and Catiofast® 8106 co-polymer were applied to the fibrous substrate samples as described above. The triggerable binder formulation add-on level of 5 wt. % for each fibrous substrate sample of the Catiofast® 8104 co-polymer, Catiofast® 8087 co-polymer, and Catiofast® 8106 co-polymer. The in-use tensile strength and disposal strength for the treated fibrous substrate samples were evaluated as described in Example 1. The treated fibrous substrate samples were allowed to equilibrate for in-use tensile strength measurements, as described above, in wetting compositions having an ethanol content of 100%, having an acetone content of 100%, and IPA content ranging from 60% to 100% as shown in Table 8 and Table 9. The treated fibrous substrate samples were soaked in the hard water for disposal strength measurements for 60 minutes. The in-use tensile strength and disposal strength measurements of the treated fibrous substrate samples are presented in Table 8 and Table 9.

TABLE 8

In-use tensile strength of TBAL fibrous substrates in various insolubilizing agents for Catiofast ® 8104 co-polymer, Catiofast ® 8087 co-polymer, and Catiofast ® 8106 co-polymer.

| Binder | Solvent | CDWT (g/in.) In-use | Std. Dev. | CDWT (g/in.) 1 hour Hard Water | Std. Dev. |
|---|---|---|---|---|---|
| Catiofast 8104 | EtOH | 297 | 16 | 13 | 18 |
| Catiofast 8104 | IPA | 431 | 17 | 28 | 10 |
| Catiofast 8104 | ACE | 389 | 49 | 20 | 13 |
| Catiofast 8087 | EtOH | 230 | 15 | 68 | 10 |
| Catiofast 8087 | IPA | 444 | 25 | 55 | 10 |
| Catiofast 8087 | ACE | 405 | 51 | 61 | 10 |
| Catiofast 8106 | EtOH | 222 | 20 | 86 | 8 |
| Catiofast 8106 | IPA | 322 | 11 | 90 | 6 |
| Catiofast 8106 | ACE | 261 | 49 | 80 | 19 |

As shown in Table 8, the in-use tensile strength and disposal strength of the treated fibrous substrate samples is a function of triggerable binder formulation type and insolubilizing agent type. Dispersibility appears to be better for lower degrees of hydrolysis of the triggerable binder formulation.

TABLE 9

In-use tensile strength of TBAL fibrous substrates for Catiofast ® 8104 co-polymer in wetting compositions having IPA content.

| % IPA | CDWT (g/in.) In-use | Std. Dev. |
|---|---|---|
| 60 | 140 | 1 |
| 70 | 144 | 8 |
| 80 | 194 | 27 |
| 90 | 328 | 13 |
| 100 | 431 | 17 |

As shown in Table 9, the in-use tensile strength of the fibrous substrate samples treated with the Catiofast® 8104 co-polymer deceases with increasing water content of the wetting composition.

EXAMPLE 8 an un-bonded air-laid fibrous substrate was prepared using CF 405 wood pulp fibers, commercially available from Weyerhaeuser (complete name/location) via an air-forming apparatus used in the art for air-laying processes. The fibrous substrate was deposited and sandwiched between two thin tissue carrier sheets to allow the fibrous substrate to be rolled into a stable roll. The width of the fibrous substrate is about 8 inches. The fibrous substrate has a basis weight of 58 gsm (±2) and caliper of 1.0 mm (±0.1). The Hercobond® polymer, as a triggerable binder formulation, was applied to the fibrous substrate as described in Example 1, with the following exceptions: square fibrous substrate samples having 8.25"×

8.25" dimensions are cut from the fibrous substrate roll; the fibrous substrate samples are carefully separated from the tissue carrier sheets and placed on a 10.25"×8.25" nylon screen; and, a rubber mask was placed over the fibrous substrate sample exposing a 7.5"×7.5" area. This assembly of the fibrous substrate sample, nylon screen, and rubber mask is placed on the stationary sample holder section of the handsheet spray unit. The triggerable binder formulation add-on level for the exposed first surface of each fibrous substrate sample was 5 wt. %. The rubber mask is removed and the fibrous substrate sample, still retained on the nylon screen, is placed in the TAD and dried at 193° C. for 30 seconds. After drying, the fibrous substrate sample is removed from the TAD. The fibrous substrate sample is removed from the nylon screen and replaced onto the nylon screen with the treated first surface in contact with the nylon screen. The rubber mask is placed on the second side of the fibrous substrate sample. The triggerable binder formulation add-on level for the exposed second surface of each fibrous substrate sample was 5 wt. %. The rubber mask is removed and the fibrous substrate sample, still retained on the nylon screen, is placed in the TAD and dried at 193° C. for 30 seconds. After drying, the fibrous substrate sample is removed from the TAD. The fibers from the un-bonded edges of the treated fibrous substrate are removed by hand. The treated fibrous substrate samples are trimmed on a laboratory cutter to provide a treated fibrous substrate sample having the dimensions of 6.5" (MD)×5.5" (CD). The total triggerable binder formulation add-on level for the treated fibrous substrate samples was 10 wt. %. The treated fibrous substrate sample has a basis weight of 65 gsm and a caliper of 1.6 mm. The dry treated fibrous substrate samples are cut into strips having. the dimensions of 1" by 4.5". The strips of the treated fibrous substrate samples are allowed to equilibrate for in-use tensile strength measurements in a wetting composition having an IPA content of 80%. The MD and CD in-use tensile strengths of the treated fibrous substrate samples were 912 g/in. (±58) and 746 g/in. (±68), respectively. The strips of the treated fibrous substrate samples are transferred to 100 ppm hard water for a 10 minute soak. Disposal strength measurements are taken after the soaking period. In both cases, the strips were too weak to accurately measure the tensile strength (>20 g/in.). In a further experiment, 6.5"×5.5" prototypes were wet with approximately 300-700% add-on level of 80% IPA. The prototype wet wipes gave excellent durability and adequate in-use properties to be used for hard surface cleaning and other applications. When the wipes were placed in a 2L beaker filled with tap water and gently stirred, they broke into small pieces and fibers in a few seconds.

EXAMPLE 9

The Baystrength® 711 polymer was evaluated as a triggerable binder formulation in a wet-laid handsheet fibrous substrate samples. The wet-laid handsheet fibrous substrate samples were prepared by dispersing 24 grams of oven-dried eucalyptus wood pulp fibers in approximately 2 liters of water. The fiber slurry was prepared through an application of 5 minutes of British Standard disintegration using equipment commercially available under the trade designation of Noram from Lorentzen and Wettre located in Pointe Claire, Quebec, and further diluted with water to a total volume of approximately 8 liters. The Baystrength® 711 polymer was added to the fiber slurry at a level of 0.3 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis. The treated wet-laid handsheet fibrous substrate samples had a basis weight of 60 gsm. The treated fibrous substrate samples were allowed to equilibrate for in-use tensile strength measurements, as described above, in aqueous or neat alcohol wetting compositions having an IPA content of between 60 and 100 percent. The in-use tensile strength of the treated fibrous substrate samples are presented in Table 10. The disposal strength of the treated fibrous substrate samples after exposure for 60 minutes soaks in 200 ppm hard water are also shown in Table 10. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 10.

EXAMPLE 10

The Baystrength® 711 polymer was evaluated as a triggerable binder formulation in a wet-laid handsheet fibrous substrate samples. The wet-laid handsheet fibrous substrate samples were prepared by dispersing 24 grams of oven-dried eucalyptus wood pulp fibers in approximately 2 liters of water. The fiber slurry was prepared through an application of 5 minutes of British Standard disintegration using the Noram equipment and further diluted with water to a total volume of approximately 8 liters. The Baystrength® 711 polymer was added to the fiber slurry at a level of 0.6 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis. The treated wet-laid handsheet fibrous substrate samples had a basis weight of 60 gsm. The treated fibrous substrate samples were allowed to equilibrate for in-use tensile strength measurements, as described above, in aqueous or neat alcohol wetting compositions having an IPA content of between 60 and 100 percent. The in-use tensile strength of the treated fibrous substrate samples are presented in Table 10. The disposal strength of the treated fibrous substrate samples after exposure for 60 minutes soaks in 200 ppm hard water are also shown in Table 10. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 10.

EXAMPLE 11

The Baystrength® 711 polymer was evaluated as a triggerable binder formulation in a wet-laid handsheet fibrous substrate samples. The wet-laid handsheet fibrous substrate samples were prepared by dispersing 24 grams of oven-dried eucalyptus wood pulp fibers in approximately 2 liters of water. The fiber slurry was prepared through an application of 5 minutes of British Standard disintegration using the Noram equipment, and further diluted with water to a total volume of approximately 8 liters. The Baystrength® 711 polymer was added to the fiber slurry at a level of 1.0 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis. The treated wet-laid handsheet fibrous substrate samples had a basis weight of 60 gsm. The treated fibrous substrate samples were allowed to equilibrate for in-use tensile strength measurements, as described above, in aqueous or neat alcohol wetting compositions having an IPA content of between 60 and 100 percent. The in-use tensile strength of the treated fibrous substrate samples are presented in Table 10. The disposal strength of the treated fibrous substrate samples after exposure for 60 minutes soaks in 200 ppm hard water are also shown in Table 10. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 10.

TABLE 10

Fibrous substrate performance for Baystrength ® 711 polymer concentration and IPA concentration in wetting compositions.

| Baystrength ® 711 Dosage (%) | IPA (%) | In-use Tensile Strength (g/in.) | Disposal Strength (g/in.) | Wet Strength Decay (%) |
|---|---|---|---|---|
| 0.3 | 60 | 147 ± 33 | 39 ± 1 | 73 |
| 0.6 | 60 | 260 ± 9 | 68 ± 9 | 74 |
| 1.0 | 60 | 362 ± 11 | 95 ± 13 | 74 |
| 0.3 | 80 | 364 ± 11 | 42 ± 12 | 88 |
| 0.6 | 80 | 500 ± 17 | 82 ± 2 | 84 |
| 1.0 | 80 | 731 ± 18 | 123 ± 6 | 83 |
| 0.3 | 100 | 1277 ± 32 | 43 ± 2 | 97 |
| 0.6 | 100 | 1665 ± 108 | 65 ± 10 | 96 |
| 1.0 | 100 | 1964 ± 128 | 97 ± 9 | 95 |

As shown in Table 10, the in-use strength and the disposal strength of the treated fibrous substrate samples are a function of concentrations of the triggerable binder formulation and insolubilizing agent.

EXAMPLE 12

The Baystrength® 711 polymer was evaluated as a triggerable binder formulation in a wet-laid handsheet fibrous substrate samples. The wet-laid handsheet fibrous substrate samples were prepared by dispersing 24 grams of oven-dried LL-19 wood pulp fibers in approximately 2 liters of water. The fiber slurry was prepared through an application of 5 minutes of British Standard disintegration using the Noram equipment and further diluted with water to a total volume of approximately 8 liters. The Baystrength® 711 polymer was added to the fiber slurry at a level of 0.3 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis. The treated wet-laid handsheet fibrous substrate samples had a basis weight of 60 gsm. The treated fibrous substrate samples were allowed to equilibrate for in-use tensile strength measurements, as described above, in aqueous alcohol wetting compositions having an IPA content of between 80 and 90 percent. The in-use tensile strength of the treated fibrous substrate samples are presented in Table 11. The disposal strength of the treated fibrous substrate samples after exposure for 60 minutes soaks in 200 ppm hard water are also shown in Table 11. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 11.

TABLE 11

Effect of wood pulp fiber type upon in-use tensile strength and disposal strength performance of fibrous substrates for Baystrength ® 711 polymer.

| Wood Fiber | IPA (%) | In-use Tensile Strength (g/in.) | Disposal Strength (g/in.) | Wet Strength Decay (%) |
|---|---|---|---|---|
| Eucalyptus | 80 | 731 ± 18 | 123 ± 6 | 83 |
| LL-19 | 80 | 828 ± 45 | 80 ± 10 | 90 |
| Eucalyptus | 85 | 1006 ± 26 | 27 ± 6 | 97 |
| LL-19 | 85 | 1238 ± 31 | 106 ± 14 | 91 |
| Eucalyptus | 90 | 1359 ± 116 | 18 ± 5 | 99 |
| LL-19 | 90 | 1505 ± 149 | 122 ± 2 | 92 |

As shown in Table 11, the in-use tensile strength and the disposal strength are a function of the wood pulp fiber type.

EXAMPLE 13

The performance of Baystrength® 711 (Example 11) was compared with Catiofast® 8104 polymer and a crosslinking, cationic polyacrylamide polymer, commercially available under the trade designation of Parez®631 polymer from Cytec Industries located in West Paterson, N.J., as triggerable binder formulations in wet-laid handsheet fibrous substrate samples. The wet-laid handsheet fibrous substrate samples were prepared by dispersing 24 grams of oven-dried eucalyptus wood pulp fibers in approximately 2 liters of water. The fiber slurry was prepared through an application of 5 minutes of British Standard disintegration using the Noram equipment, and further diluted with water to a total volume of approximately 8 liters. The Parez® 631 or Catiofast® 8104 polymers were added to the fiber slurry at a level of 1.0 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis. The treated wet-laid handsheet fibrous substrate samples had a basis weight of 60 gsm. The treated fibrous substrate samples were allowed to equilibrate for in-use tensile strength measurements, as described above, in aqueous or neat alcohol wetting compositions having an IPA content of between 60 and 100 percent. The in-use tensile strength of the treated fibrous substrate samples are presented in Table 12. The disposal strength of the treated fibrous substrate samples after exposure for 60 minutes soaks in 200 ppm hard water are also shown in Table 12. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 12.

TABLE 12

Comparison of Baystrength ® 711 polymer with Parez ® 631 polymer and Catiofast ® 8104 polymer on wet-laid handsheet fibrous substrates in 60% to 100% IPA wetting compositions.

| Polymer | IPA (%) | In-use Tensile Strength (g/in.) | Disposal Strength (g/in.) | Wet Strength Decay (%) |
|---|---|---|---|---|
| Parez ® 631 | 60 | 379 ± 9 | 244 ± 91 | 36 |
| Baystrength ® 711 | 60 | 362 ± 11 | 95 ± 13 | 74 |
| Catiofast ® 8104 | 60 | 165 ± 18 | 0 | 100 |
| Parez ® 631 | 80 | 794 ± 154 | 194 ± 45 | 76 |
| Baystrength ® 711 | 80 | 731 ± 18 | 123 ± 6 | 83 |
| Catiofast ® 8104 | 80 | 367 ± 14 | 0 | 100 |
| Parez ® 631 | 100 | 2562 ± 103 | 174 ± 42 | 93 |
| Baystrength ® 711 | 100 | 1964 ± 128 | 97 ± 9 | 95 |
| Catiofast ® 8104 | 100 | 1301 ± 99 | 0 | 100 |

As shown in Table 12, the in-use tensile strength and the disposal strength are a function of the triggerable binder formulation type and of the concentrations of the triggerable binder formulation and the insolubilizing agent.

EXAMPLE 14

The performance of the Baystrength® 711 polymer was evaluated as a triggerable binder formulation on wet-laid, 40 gsm handsheet fibrous substrate samples. One set of wet-laid handsheet fibrous substrate samples were prepared by dispersing 16 grams of oven-dried eucalyptus wood pulp fibers in approximately 2 liters of water. The fiber slurry was prepared through an application of 5 minutes of British Standard disintegration using the Noram equipment, and further diluted with water to a total volume of approximately 8 liters. The Baystrength® 711 polymer was added to the fiber slurry at a level of 2.0 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis.

Another set of wet-laid handsheet fibrous substrate samples were prepared by dispersing 16 grams of oven-dried LL-19 wood pulp fibers in approximately 2 liters of water. The fiber slurry was prepared through an application of 5 minutes of British Standard disintegration using the Noram equipment, and further diluted with water to a total volume of approximately 8 liters. The Baystrength® 711 polymer was added to the fiber slurry at a level of 2.0 weight percent based upon final fibrous substrate composition. The treated wet-laid handsheet fibrous substrate samples were created in a forming mold, pressed for one minute at a pressure of 98 psi, and dried for two minutes on a steam dryer at 105° C. using handsheet equipment commercially available from Voith Incorporated located in Appleton, Wis.

Both sets of treated fibrous substrate samples were allowed to equilibrate for in-use tensile strength measurements, as described above, in aqueous or neat alcohol wetting compositions having an IPA content of between 80 and 100 percent. The in-use tensile strength of the treated fibrous substrate samples are presented in Table 13. The disposal strength of the treated fibrous substrate samples after exposure for 60 minutes soaks in 200 ppm hard water are also shown in Table 13. The wet strength decay was calculated for each of the treated fibrous substrate samples by dividing the difference of the in-use tensile strength and the disposal strength by the in-use tensile strength for a given treated fibrous substrate sample. The wet strength decay values are presented in Table 13.

TABLE 13

Effect of wood pulp fiber type upon in-use tensile strength and disposal strength performance of fibrous substrates for Baystrength ® 711 polymer.

| Wood Fiber | IPA (%) | In-use Tensile Strength (g/in.) | Disposal Strength (g/in.) | Wet Strength Decay (%) |
|---|---|---|---|---|
| Eucalyptus | 80 | 615 ± 40 | 0 | 100 |
| LL-19 | 80 | 775 ± 66 | 93 ± 11 | 88 |
| Eucalyptus | 85 | 806 ± 114 | 0 | 100 |
| LL-19 | 85 | 928 ± 125 | 80 ± 5 | 91 |
| Eucalyptus | 90 | 1054 ± 151 | 0 | 100 |
| LL-19 | 90 | 1231 ± 121 | 68 ± 20 | 94 |
| Eucalyptus | 95 | 1476 ± 111 | 0 | 100 |
| LL-19 | 95 | 1699 ± 143 | 75 ± 9 | 96 |
| Eucalyptus | 100 | 1711 ± 366 | 0 | 100 |
| LL-19 | 100 | 2398 ± 251 | 45 ± 13 | 98 |

As shown in Table 13, the in-use tensile strength and the disposal strength are a function of wood pulp fiber type.

EXAMPLE 15

In this Example, insolubilizing agents comprising one or more polyols were evaluated as wetting compositions on the TBAL fibrous substrate samples prepared according to the method described in Example 1. The triggerable binder formulation (Hercobond® 2000, Hercules, Inc., Wilmington, Del.) was added to the TBAL fibrous substrate samples at an add-on level of 5-10 wt. %. The treated TBAL fibrous substrate samples were allowed to soak overnight for in-use tensile strength measurements, as described above, in a wetting composition having a polyol content of 100%. Polyols used as insolubilizing agents in this Example were: 100% propylene glycol, 100% polyethylene glycol 400, and 50% propylene glycol+50% polyethylene glycol 400. The "in-use" tensile strength and "disposal" strength following 10 minutes in water for the treated fibrous substrate samples were evaluated as described in Example 1, and the results are presented in Table 14.

TABLE 14

Effect of wetting compositions comprising one or more polyols upon in-use tensile strength and disposal strength performance of fibrous substrates for Hercobond ® 2000 polymer.

| Polyol Wetting Composition | "In-Use" MDWT (g/in.) | "Disposal" MDWT (g/in.) |
|---|---|---|
| 100% propylene glycol | 1517 ± 17 | <30 |
| 100% polyethylene glycol 400 | 2264 ± 203 | <30 |
| 50% propylene glycol + 50% polyethylene glycol 400 | 1812 ± 68 | <30 |

As shown in Table 14, the propylene glycol, polyethylene glycol 400, and mixtures thereof are suitable for use as an insolubilizing agent in the wetting composition to wet the wet wipe of the present invention.

EXAMPLE 16

In this Example, anti-microbial agents were evaluated as additives to the wetting composition used to wet the wet wipes of the present invention. The microbial sample solutions were prepared by transferring one loopful of *Escherichia coli* (ATCC #8739, American Type Culture Collection, Manassas, Va.) and *Staphylococcus aureus* (ATCC #6538, American Type Culture Collection, Manassas, Va.) into 10 mL of fresh Tripticase Soy Broth (TSB, BBL prepared culture media, Becton, Dickinson and Co., Sparks, Md.) and one loopful of *Candida albicans* (ATCC #10231, American Type Culture Collection, Manassas, Va.) into 10 mL of fresh Sabauroud Dextrose Broth (SAB-DEX, Difco Media, Becton, Dickinson and Co., Sparks, Md.). Cultures were transferred daily for a minimum of three days prior to use, and cultures were not transferred for longer than two weeks. The cultures were incubated overnight at 37° C. (±2° C.) in an incubator/shaker (Innova 4000, New Brunswick Scientific, New Brunswick, N.J.) with continuous shaking at 200 rpm.

UCTAD tissue was prepared according to the method described in Example 1. The triggerable binder formulation (Hercobond® 2000, Hercules, Inc., Wilmington, Del.) was added to the TBAL fibrous substrate samples at an add-on level of 5 wt. %. For each wetting composition sample, three sample tissues were cut into 8 millimeter diameter discs with a #4 punch. Sample tissues were also cut for negative control purposes. The sample tissues were wet with 7.0 μL of each wetting composition sample and held in a sterile petri dish. The negative control tissues were wet with either water or sterile phosphate buffered saline (PBS). Test plates of solid media (TSB or SAB-DEX agar) were inoculated with a solid lawn of the broth cultures of the microbial samples. The plates were swabbed in a cross-hatch pattern, and each plate was marked into four quadrants with a marker.

Immediately following inoculation, the three sample tissues wet with the wetting composition samples were placed on three of the four quadrants, with the negative control tissue sample placed on the fourth quadrant. The plates were inverted and incubated for 24 hours at 37° C. (±2° C.). Following the overnight incubation, the plates were analyzed for the presence or absence of a "zone of inhibition," i.e., a clear ring with no microbial growth around the edge of the tissue sample discs. The zone of inhibition was recorded as the diameter in millimeters of the clear zone minus the diameter of the zone of the disc (8 millimeters). Results of the average zone of inhibition each wetting composition sample was able to elicit for three microbial samples are presented in Table 15, below.

TABLE 15

Zone of Inhibition Trials for the Wetting Composition Comprising Anti-Microbials.

| Wetting Composition Sample | Zone of Inhibition (millimeters) for Each Microbial Sample | | |
|---|---|---|---|
| | Candida albicans | Escherichia coli | Staphylococcus aureus |
| TRIAL 1 | | | |
| 80% Isopropyl alcohol (IPA) in water | 0.3 ± 0.29 | 0.7 ± 0.29 | 0.8 ± 0.29 |

TABLE 15-continued

Zone of Inhibition Trials for the Wetting Composition Comprising Anti-Microbials.

| Wetting Composition Sample | Zone of Inhibition (millimeters) for Each Microbial Sample | | |
|---|---|---|---|
| | Candida albicans | Escherichia coli | Staphylococcus aureus |
| 80% IPA + 0.5% iodine in water | 14.7 ± 2.08 | 3.3 ± 0.58 | 7.7 ± 0.58 |
| 80% IPA + 3% $H_2O_2$ in water | 5.3 ± 0.58 | 7.3 ± 1.53 | 21.3 ± 3.51 |
| 80% IPA + 0.5% sodium hypochloride in water | 2.7 ± 1.53 | 0.5 ± 0.00 | 1.7 ± 0.58 |
| 80% IPA + 0.1% benzalkonium chloride in water | 2.7 ± 2.08 | 1.5 ± 0.87 | 8.3 ± 1.53 |
| 80% IPA + 0.1% benzethonium chloride in water | 3.0 ± 1.00 | 1.3 ± 0.58 | 8.3 ± 0.58 |
| 100% Sterile PBS | 0.0 ± 0.00 | 0.0 ± 0.00 | 0.0 ± 0.00 |
| TRIAL 2 | | | |
| 80% Isopropyl alcohol (IPA) in water | 0.0 | 0.5 | 0.5 |
| 80% IPA + 3% $H_2O_2$ in water | 4.0 | 6.0 | 15.0 |
| 3% $H_2O_2$ in water | 7.3 ± 0.58 | 8.0 ± 1.00 | 18.3 ± 2.89 |
| 2% $H_2O_2$ in water | 6.0 ± 1.00 | 7.3 ± 1.15 | 15.0 ± 2.65 |
| 1% $H_2O_2$ in water | 3.0 ± 1.00 | 4.3 ± 1.15 | 10.0 ± 3.61 |
| 100% water | 0.0 ± 0.00 | 0.0 ± 0.00 | 0.0 ± 0.00 |
| TRIAL 3 | | | |
| 80% Isopropyl alcohol (IPA) in water | 0.0 ± 0.00 | 0.0 ± 0.00 | 0.5 ± 0.00 |
| 3% $H_2O_2$ in water | 6.0 ± 1.00 | 8.3 ± 1.15 | 19.3 ± 1.53 |
| 2% $H_2O_2$ in water | 4.0 ± 0.00 | 5.3 ± 1.15 | 11.7 ± 4.93 |
| 1% $H_2O_2$ in water | 1.3 ± 0.58 | 4.0 ± 1.00 | 9.0 ± 4.36 |
| 80% IPA + 3% $H_2O_2$ in water | 8.3 ± 0.58 | 9.3 ± 1.53 | 21.7 ± 2.31 |
| 80% IPA + 2% $H_2O_2$ in water | 5.0 ± 1.00 | 6.7 ± 1.15 | 15.3 ± 2.52 |
| 80% IPA + 1% $H_2O_2$ in water | 3.7 ± 0.58 | 6.0 ± 1.00 | 17.3 ± 1.53 |
| 100% water | 0.0 ± 0.00 | 0.0 ± 0.00 | 0.0 ± 0.00 |

Following the three experimental trials, data were compiled to determine whether there was synergistic zone of inhibition between the isopropyl alcohol and the anti-microbial hydrogen peroxide separately and together. The most promising zone of inhibition values (in millimeters) for 80% IPA in wetting composition samples and 1%, 2%, and 3% hydrogen peroxide wetting compositions were selected. These values were added together to create the "theoretical" zone of inhibition. Then, those values were compared with the zone of inhibition value (in millimeters) for wetting composition samples of 80% IPA+1%, 2%, and 3% hydrogen peroxide, to determine if there was actual synergy between the two compositions. Where the zone of inhibition for the 80% IPA and hydrogen peroxide combined was greater than the "theoretical" zone of inhibition, actual synergy was achieved. Results of the synergy determinations are presented in Table 16, below.

TABLE 16

Zone of Inhibition Synergy determination of certain wetting compositions comprising an insolubilizing agent and an anti-microbial.

| Wetting Composition Sample | Candida albicans Theoretical IPA + $H_2O_2$ | Candida albicans Actual Synergy | Escherichia coli Theoretical IPA + $H_2O_2$ | Escherichia coli Actual Synergy | Staphylococcus aureus Theoretical IPA + $H_2O_2$ | Staphylococcus aureus Actual Synergy |
|---|---|---|---|---|---|---|
| 80% IPA + 3% $H_2O_2$ in water | 3.3 | 3.7 | 5.0 | 6.0 | 10.8 | 17.3 |
| 80% IPA + 2% $H_2O_2$ in water | 6.3 | 5.0 | 8.0 | 6.7 | 15.8 | 15.3 |
| 80% IPA + 1% $H_2O_2$ in water | 7.7 | 8.3 | 8.7 | 9.3 | 19.2 | 21.7 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A wet wipe product comprising a fibrous substrate material, a triggerable binder formulation, and a wetting composition comprising from about 50% to about 100% by weight of an insolubilizing agent in contact with the fibrous substrate material, wherein the triggerable binder formulation is insoluble in the wetting composition and dispersible in disposal water having 500 or greater parts per million of calcium and magnesium ions and is selected from the group consisting of acrylamide polymers and polymer formulations, vinylamide/amine polymers and polymer formulations, and mixtures thereof, and wherein the insolubilizing agent comprises at least one polyol.

2. The wet wipe product of claim 1 wherein the polyol increases in temperature upon exposure to moisture.

3. The wet wipe product of claim 1 wherein the fibrous substrate material has a triggerable binder formulation add-on level of about 0.1 wt. % to about 25 wt. %.

4. The wet wipe product of claim 1 wherein the polyol is a polyhydric alcohol selected from the group consisting of polyalkylene glycol, glycerol, diglycerol, polyglycerol, butylene glycol, propylene glycol, dipropylene glycol, polypropylene glycol, hexylene glycol, polyethylene glycol, trimethylene glycol, PEGylated compounds, block copolymers comprising polkalkylene glycol, erythritol, pentaerythritol, sorbitan, glucose, sorbitol, malitol, sucrose, raffinose, trehalose, and mixtures thereof.

5. The wet wipe product of claim 1 wherein the polyol is selected from the group consisting of propylene glycol, polyethylene glycol 300, polyethylene glycol 400, and mixtures thereof.

6. The wet wipe product of claim 1 wherein the triggerable binder formulation is a polymerization product comprising acrylamide or vinylamide/amine monomers and, optionally, at least one monomer selected from the group consisting of acrylic acid, methacrylic acid and their salts, 2-acrylamido-2-methyl-1 propanesulfonic acid and its salts, vinyl sulfonic acid and their salts, and sulfonate monomers.

7. The wet wipe product of claim 1 wherein the triggerable binder formulation is a polymerization product comprising acrylamide or vinylamide/amine monomers and, optionally, at least one monomer selected from the group consisting of [2-(acryloxy)ethyl] trimethyl ammonium chloride, [2-(methacryloxy)ethyl] trimethyl ammonium chloride, (3-acrylamidopropyl) trimethyl ammonium chloride, N,N-diallyldimethyl ammonium chloride, [2-(acryloxy) ethyl] dimethylbenzyl ammonium chloride, [2-(methacryloxy) ethyl] dimethylbenzyl ammonium chloride, [2-(acryloxy) ethyl] dimethyl ammonium chloride, and [2-(methacryloxy) ethyl] dimethyl ammonium chloride.

8. The wet wipe product of claim 1 wherein the wet wipe product has an in-use tensile strength of about 300 g/in. or greater.

9. The wet wipe product of claim 1 wherein the wet wipe product has a disposal strength of about 75 g/in. or less.

10. The wet wipe product of claim 1 wherein the fibrous substrate material is air-laid, wet-laid, or is a coform product.

11. The wet wipe product of claim 1 wherein the wetting composition further comprises at least one additional ingredient selected from the group consisting of anti-microbial agents, hormones, antibiotics, anesthetics, analgesics, immunodilators, contraceptives, odor control additives, microparticulates, microcapsules, preservatives, wetting agents, cleaning agents, surface feel modifiers, fragrances, fragrance, solubilizers, opacifiers, and pH control agents.

12. The wet wipe product of claim 11 wherein the anti-microbial agent is an anti-fungal agent.

13. The wet wipe product of claim 12 wherein the anti-fungal agent is selected from the group consisting of miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole, ternafine, naftifine, amorolfine, butenafine, ciclopirox, griseofulvin, undecyclenic acid, haloprogin, tolnaftate, nystatin, iodine, rilopirox, BAY 108888, purpuromycin, their pharmaceutically acceptable salts, and mixtures thereof.

14. The wet wipe product of claim 11 wherein the anti-microbial agent is an anti-bacterial agent.

15. The wet wipe product of claim 14 wherein the anti-bacterial agent is selected from the group consisting of chlorohexidine gluconate, sodium polystyrene sulfonate, sodium cellulose sulfate, silver particles, silver salts, and mixtures thereof.

16. The wet wipe product of claim 11 wherein the anti-microbial agent is an anti-viral agent.

17. The wet wipe product of claim 16 wherein the anti-viral agent is selected from the group consisting of imiquimod, imiquimod derivatives, podofilox, podophyllin, interferon alpha, reticolos, cidofovir, nonoxynol-9, their pharmaceutically acceptable salts, and mixtures thereof.

18. The wet wipe product of claim 11 wherein the anti-microbial agent is an antiseptic agent.

19. The wet wipe product of claim 18 wherein the antiseptic agent is selected from the group consisting of quaternary ammonium compounds, mercury compounds, and iodine compounds.

20. The wet wipe product of claim 18 wherein the antiseptic agent is selected from the group consisting of benzalkonium chloride, benzethonium chloride, cetrimide, chlorhexidine, hexachlorophene, alcohol, hydrogen peroxide, hexamine hippurate, triclosan, cetylpyridinium chloride, dequalinium chloride, and mixtures thereof.

21. A wet wipe product comprising a fibrous substrate material, a triggerable binder formulation, and a wetting composition comprising from about 50% to about 100% by weight of an insolubilizing agent in contact with the fibrous substrate material, wherein the triggerable binder formulation is insoluble in the wetting composition and dispersible in disposal water having 500 or greater parts per million of calcium and magnesium ions and is selected from the group consisting of acrylamide polymers and polymer formulations, vinyl/amine polymers and polymer formulations, and mixtures thereof, and wherein the insolubilizing agent comprises one or more compounds selected from the group consisting of polyols, lower alcohols, lower glycols, lower ketones, and mixtures thereof, and wherein the wetting composition further comprises an anti-microbial agent.

22. The wet wipe product of claim 21 wherein the polyol increases in temperature upon exposure to moisture.

23. The wet wipe product of claim 21 wherein the fibrous substrate material has a triggerable binder formulation add-on level of about 0.1 wt. % to about 25 wt. %.

24. The wet wipe product of claim 21 wherein the polyol is a polyhydric alcohol selected from the group consisting of polyalkylene glycol, glycerol, diglycerol, polyglycerol, butylene glycol, propylene glycol, dipropylene glycol, polypropylene glycol, hexylene glycol, polyethylene glycol, trimethylene glycol, PEGylated compounds, block copolymers comprising polkalkylene glycol, erythritol, pentaerythritol, sorbitan, glucose, sorbitol, malitol, sucrose, raffinose, trehalose, and mixtures thereof.

25. The wet wipe product of claim 21 wherein the polyol is selected from the group consisting of propylene glycol, polyethylene glycol 300, polyethylene glycol 400, and mixtures thereof.

26. The wet wipe product of claim 21, wherein the lower alcohol, lower glycol, or lower ketone is selected from the group consisting of methyl alcohol, ethyl alcohol, n-propyl alcohol, isopropyl alcohol, n-butyl alcohol, sec-butyl alcohol, tert-butyl alcohol, ethylene glycol, 1,2 propandiol (propylene glycol), 1,3 propane diol, acetone, methylethyl ketone, and mixtures thereof.

27. The wet wipe product of claim 21 wherein the triggerable binder formulation is a polymerization product comprising acrylamide or vinylamide/amine monomers and, optionally, at least one monomer selected from the group comprising acrylic acid, methacrylic acid and their salts, 2-acrylamido-2-methyl-1 propanesulfonic acid and its salts, vinyl sulfonic acid and their salts, and sulfonate monomers.

28. The wet wipe product of claim 21 wherein the triggerable binder formulation is a polymerization product comprising acrylamide or vinylamide/amine monomers and, optionally, at least one monomer selected from the group consisting of [2-(acryloxy)ethyl] trimethyl ammonium chloride, [2-(methacryloxy)ethyl] trimethyl ammonium chloride, (3-acrylamidopropyl) trimethyl ammonium chloride, N,N-diallyldimethyl ammonium chloride, [2-(acryloxy) ethyl] dimethylbenzyl ammonium chloride, [2-(methacryloxy) ethyl] dimethylbenzyl ammonium chloride, [2-(acryloxy) ethyl] dimethyl ammonium chloride, and [2-(methacryloxy) ethyl] dimethyl ammonium chloride.

29. The wet wipe product of claim 21 wherein the wet wipe product has an in-use tensile strength of about 300 g/in. or greater.

30. The wet wipe product of claim 21 wherein the wet wipe product has a disposal strength of about 75 g/in. or less.

31. The wet wipe product of claim 21 wherein the fibrous substrate material is air-laid, wet-laid, or is a coform product.

32. The wet wipe product of claim 21 wherein the anti-microbial agent is an anti-fungal agent.

33. The wet wipe product of claim 32 wherein the anti-fungal agent is selected from the group consisting of miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole, ternafine, naftifine, amorolfine, butenafine, ciclopirox, griseofulvin, undecyclenic acid, haloprogin, tolnaftate, nystatin, iodine, rilopirox, BAY 108888, purpuromycin, their pharmaceutically acceptable salts, and mixtures thereof.

34. The wet wipe product of claim 21 wherein the anti-microbial agent is an anti-bacterial agent.

35. The wet wipe product of claim 34 wherein the anti-bacterial agent is selected from the group consisting of chlorohexidine gluconate, sodium polystyrene sulfonate, sodium cellulose sulfate, silver particles, silver salts, and mixtures thereof.

36. The wet wipe product of claim 21 wherein the anti-microbial agent is an anti-viral agent.

37. The wet wipe product of claim 36 wherein the anti-viral agent is selected from the group consisting of imiquimod, imiquimod derivatives, podofilox, podophyllin, interferon alpha, reticolos, cidofovir, nonoxynol-9, their pharmaceutically acceptable salts, and mixtures thereof.

38. The wet wipe product of claim 21 wherein the anti-microbial agent is an antiseptic agent.

39. The wet wipe product of claim 38 wherein the antiseptic agent is selected from the group consisting of quaternary ammonium compounds, mercury compounds, and iodine compounds.

40. The wet wipe product of claim 38 wherein the antiseptic agent is selected from the group consisting of benzalkonium chloride, benzethonium chloride, cetrimide, chlorhexidine, hexachlorophene, alcohol, hydrogen peroxide, hexamine hippurate, triclosan, cetylpyridinium chloride, dequalinium chloride, and mixtures thereof.

* * * * *